(12) United States Patent
Wyss et al.

(10) Patent No.: US 8,202,323 B2
(45) Date of Patent: Jun. 19, 2012

(54) KNEE PROSTHESES WITH ENHANCED KINEMATICS

(75) Inventors: Joseph G. Wyss, Fort Wayne, IN (US);
John L. Williams, Fort Wayne, IN (US);
Said T. Gomaa, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 508 days.

(21) Appl. No.: 12/174,539

(22) Filed: Jul. 16, 2008

(65) Prior Publication Data

US 2010/0016979 A1 Jan. 21, 2010

(51) Int. Cl.
*A61F 2/30* (2006.01)
*A61F 2/38* (2006.01)

(52) U.S. Cl. ............... 623/20.21; 623/20.28; 623/20.29; 623/20.31; 623/20.14; 623/18.11

(58) Field of Classification Search ..... 623/20.14–20.23
See application file for complete search history.

(56) References Cited

U.S. PATENT DOCUMENTS

| | | | |
|---|---|---|---|
| 3,869,731 A | 3/1975 | Waugh et al. | |
| 4,209,861 A | 7/1980 | Walker et al. | |
| 4,215,439 A | 8/1980 | Gold et al. | |
| 4,340,978 A | 7/1982 | Buechel et al. | |
| 4,470,158 A | 9/1984 | Pappas et al. | |
| 4,888,021 A | 12/1989 | Forte et al. | |
| 5,007,933 A * | 4/1991 | Sidebotham et al. | 623/20.27 |
| 5,071,438 A | 12/1991 | Jones et al. | |
| 5,133,758 A | 7/1992 | Hollister | |
| 5,147,405 A * | 9/1992 | Van Zile et al. | 623/20.27 |
| 5,219,362 A | 6/1993 | Tuke et al. | |
| 5,326,361 A | 7/1994 | Hollister | |
| 5,330,533 A | 7/1994 | Walker | |
| 5,344,460 A | 9/1994 | Turanyi et al. | |
| 5,370,699 A * | 12/1994 | Hood et al. | 623/20.28 |

(Continued)

FOREIGN PATENT DOCUMENTS

DE 19529824 A1 2/1997

(Continued)

OTHER PUBLICATIONS

European Patent Office, Search Report for App. No. 09164479.9-2310, mailed Nov. 4, 2009, 3 pages.

(Continued)

*Primary Examiner* — David Isabella
*Assistant Examiner* — Jacqueline Woznicki
(74) *Attorney, Agent, or Firm* — Maginot, Moore & Beck, LLP

(57) ABSTRACT

A knee replacement system includes a proximal tibial posterior camming portion defined by a first radius of curvature with a first origin in a first medio-lateral plane, a distal tibial posterior camming portion defined by a second radius of curvature with a second origin in a second medio-lateral plane, an anterior femoral camming portion of a posterior cam defined by a third radius of curvature with a third origin in the first medio-lateral plane, and a posterior femoral camming portion of the posterior cam and defined by a fourth radius of curvature with a fourth origin in the second medio-lateral plane, wherein the second origin is closer to the lateral tibial portion than the first origin, or the fourth origin is closer to the medial femoral portion than the third origin.

23 Claims, 15 Drawing Sheets

U.S. PATENT DOCUMENTS

| | | | |
|---|---|---|---|
| 5,387,240 | A | 2/1995 | Pottenger et al. |
| 5,395,401 | A | 3/1995 | Bahler |
| 5,413,604 | A | 5/1995 | Hodge |
| 5,549,686 | A | 8/1996 | Johnson et al. |
| 5,571,194 | A | 11/1996 | Gabriel |
| 5,609,643 | A | 3/1997 | Colleran et al. |
| 5,639,279 | A | 6/1997 | Burkinshaw et al. |
| 5,658,342 | A | 8/1997 | Draganich et al. |
| 5,681,354 | A * | 10/1997 | Eckhoff ............... 623/20.35 |
| 5,683,468 | A | 11/1997 | Pappas |
| 5,702,458 | A * | 12/1997 | Burstein et al. ........ 623/20.31 |
| 5,702,466 | A | 12/1997 | Pappas et al. |
| 5,755,801 | A | 5/1998 | Walker et al. |
| 5,776,201 | A | 7/1998 | Colleran et al. |
| 5,800,552 | A | 9/1998 | Forte |
| 5,824,100 | A | 10/1998 | Kester et al. |
| 5,824,102 | A | 10/1998 | Buscayret |
| 5,871,543 | A | 2/1999 | Hofmann |
| 5,871,546 | A | 2/1999 | Colleran et al. |
| 5,935,173 | A | 8/1999 | Roger et al. |
| 5,997,577 | A * | 12/1999 | Herrington et al. ...... 623/20.15 |
| 6,004,351 | A | 12/1999 | Tomita et al. |
| 6,013,103 | A | 1/2000 | Kaufman et al. |
| 6,039,764 | A | 3/2000 | Pottenger et al. |
| 6,080,195 | A * | 6/2000 | Colleran et al. ........ 623/20.32 |
| 6,123,729 | A | 9/2000 | Insall et al. |
| 6,206,926 | B1 | 3/2001 | Pappas |
| 6,264,697 | B1 * | 7/2001 | Walker ............... 623/20.27 |
| 6,299,646 | B1 | 10/2001 | Chambat et al. |
| 6,325,828 | B1 * | 12/2001 | Dennis et al. ........... 623/20.14 |
| 6,344,059 | B1 | 2/2002 | Krakovits et al. |
| 6,379,388 | B1 | 4/2002 | Ensign et al. |
| 6,443,991 | B1 | 9/2002 | Running |
| 6,475,241 | B2 | 11/2002 | Pappas |
| 6,491,726 | B2 | 12/2002 | Pappas |
| 6,540,787 | B2 | 4/2003 | Biegun et al. |
| 6,589,283 | B1 | 7/2003 | Metzger et al. |
| 6,730,128 | B2 * | 5/2004 | Burstein ................. 623/20.27 |
| 6,764,516 | B2 | 7/2004 | Pappas |
| 6,770,099 | B2 | 8/2004 | Andriacchi et al. |
| 6,797,005 | B2 | 9/2004 | Pappas |
| 6,846,329 | B2 | 1/2005 | McMinn |
| 6,893,467 | B1 | 5/2005 | Bercovy |
| 6,916,340 | B2 | 7/2005 | Metzger et al. |
| 6,926,738 | B2 | 8/2005 | Wyss |
| 6,972,039 | B2 * | 12/2005 | Metzger et al. ........ 623/20.29 |
| 6,986,791 | B1 | 1/2006 | Metzger |
| 7,066,963 | B2 | 6/2006 | Naegerl |
| 7,081,137 | B1 | 7/2006 | Servidio |
| 7,105,027 | B2 | 9/2006 | Lipman et al. |
| 7,160,330 | B2 * | 1/2007 | Axelson et al. ........ 623/20.14 |
| 7,261,740 | B2 | 8/2007 | Tuttle et al. |
| 7,326,252 | B2 * | 2/2008 | Otto et al. ............. 623/20.15 |
| 7,422,605 | B2 | 9/2008 | Burstein et al. |
| 7,658,767 | B2 * | 2/2010 | Wyss ................. 623/20.29 |
| 7,678,152 | B2 | 3/2010 | Suguro et al. |
| 7,842,093 | B2 | 11/2010 | Peters et al. |
| 2003/0009232 | A1 * | 1/2003 | Metzger et al. ........ 623/20.29 |
| 2004/0243244 | A1 | 12/2004 | Otto et al. |
| 2004/0243245 | A1 | 12/2004 | Plumet et al. |
| 2005/0143832 | A1 * | 6/2005 | Carson ............... 623/20.28 |
| 2005/0154472 | A1 | 7/2005 | Afriat |
| 2006/0178749 | A1 | 8/2006 | Pendleton et al. |
| 2007/0135926 | A1 | 6/2007 | Walker |
| 2008/0269596 | A1 | 10/2008 | Revie et al. |
| 2009/0043396 | A1 | 2/2009 | Komistek |
| 2009/0306785 | A1 | 12/2009 | Farrar et al. |
| 2009/0326663 | A1 * | 12/2009 | Dun .................. 623/20.21 |

FOREIGN PATENT DOCUMENTS

| | | |
|---|---|---|
| EP | 1440675 | 7/2004 |
| EP | 1591082 | 11/2005 |
| FR | 2621243 A1 | 4/1989 |
| FR | 2787012 A1 | 6/2000 |
| FR | 2835178 A1 | 8/2003 |
| WO | 0209624 A1 | 7/2002 |
| WO | 2004058108 | 7/2004 |
| WO | 2007119173 A2 | 10/2007 |

OTHER PUBLICATIONS

Barnes, C.L., et al, "Kneeling is Safe for Patients Implanted With Medial-Pivot Total Knee Arthroplasty Designs, Journal of Arthroplasty," vol. 00, No. 0 2010, 1-6, 6 pages.

Blaha, et al., "Kinematics of the Human Knee Using an Open Chain Cadaver Model", Clinical Orthopaedics and Related Research, Vol. 410 (2003); 25-34, 10 pages.

Dennis, et al., "A Multi-Center Analysis of Axial Femorotibial Rotation After Total Knee Arthroplasty", Clinical Orthopaedics 428 (2004): 180-189, 10 pages.

Fan, Cheng-Yu, et al, "Primitive Results After Medial-Pivot Knee Arthroplasties: A Minimum 5-Year Follow-Up Study," The Journal of Arthroplasty, Vol. 25, No. 3 2010, 492-496, 5 pages.

Freeman, M.A.R., et al, "The Movement of the Normal Tibio-Femoral Joint," The Journal of Biomechanics 38 (2005) (2), pp. 197-208, 12 pgs.

Fuller, et al., "A Comparison of Lower-Extremity Skeletal Kinematics Measured Using Skinand Pin-Mounted Markers", Human Movement Science 16 (1997) 219-242, 24 pages.

Hill, et al., "Tibiofemoral Movement 2: The Loaded and Unloaded Living Knee Studied by MRI", The Journal of Bone & Joint Surgery, vol. 82-B, No. 8 (Nov. 2000), 1196-1198, 3 pages.

Karachalios, et al., "A Mid-Term Clinical Outcome Study of the Advance Medial Pivot Knee Arthroplasty," Www.Sciencedirect.Com, the Knee 16 (2009); 484-488, 5 pages.

Komistek, et al., "In Vivo Flouroscopic Analysis of the Normal Human Knee", Clinical Orthopaedics 410 (2003): 69-81, 13 pages.

Komistek, et al., "In Vivo Polyethylene Bearing Mobility Is Maintained in Posterior Stabilized Total Knee Arthroplasty", Clinical Orthopaedics 428 (2004): 207-213, 7 pages.

Koo, et al., "The Knee Joint Center of Rotation is Predominantly on the Lateral Side During Normal Walking", Journal of Biomechanics, vol. 41 (2008): 1269-1273, 5 pages.

Kurosawa, et al., "Geometry and Motion of the Knee for Implant and Orthotic Design", The Journal of Biomechanics 18 (1985), pp. 487-499, 12 pages.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 pages.

Moonot, et al., "Correlation Between the Oxford Knee and American Knee Society Scores at Mid-Term Follow-Up", The Journal of Knee Surgery, vol. 22, No. 3 (Jul. 2009), 226-230, 5 pages.

Murphy, Michael Charles, "Geometry and the Kinematics of the Normal Human Knee", Submitted to Masachusetts Institute of Technology (1990), 381 pages.

Nakagawa, et al., "Tibiofemoral Movement 3: Full Flexion of the Normal Human Knee", J.Bone Joint Surg. Am, vol. 82-B, No. 8 (2000), 1199-1200, 2 pages.

Omori, et al., "The Effect of Geometry of the Tibial Polyethylene Insert on the Tibiofemoral Contact Kinematics in Advance Medial Pivot Total Knee Arthroplasty", The Journal of Orthopaedics Science (2009) 14:754-760, 7 pages.

Shakespeare, et al., "Flexion After Total Knee Replacement. A Comparison Between the Medial Pivot Knee and a Posterior Stabilised Knee," www.sciencedirect.com, The Knee 13 (2006): 371-372, 3 pages.

Shaw et al., "The Longitudinal Axis of the Knee and the Role of the Cruciate Ligaments in Controlling Transverse Rotation," J.Bone Joint Surg. Am. 1974:56:1603-1609, 7 pages.

Walker, et al., "Motion of a Mobile Bearing Knee Allowing Translation and Rotation", Journal of Arthroplasty 17 (2002): 11-19, 9 pages.

* cited by examiner

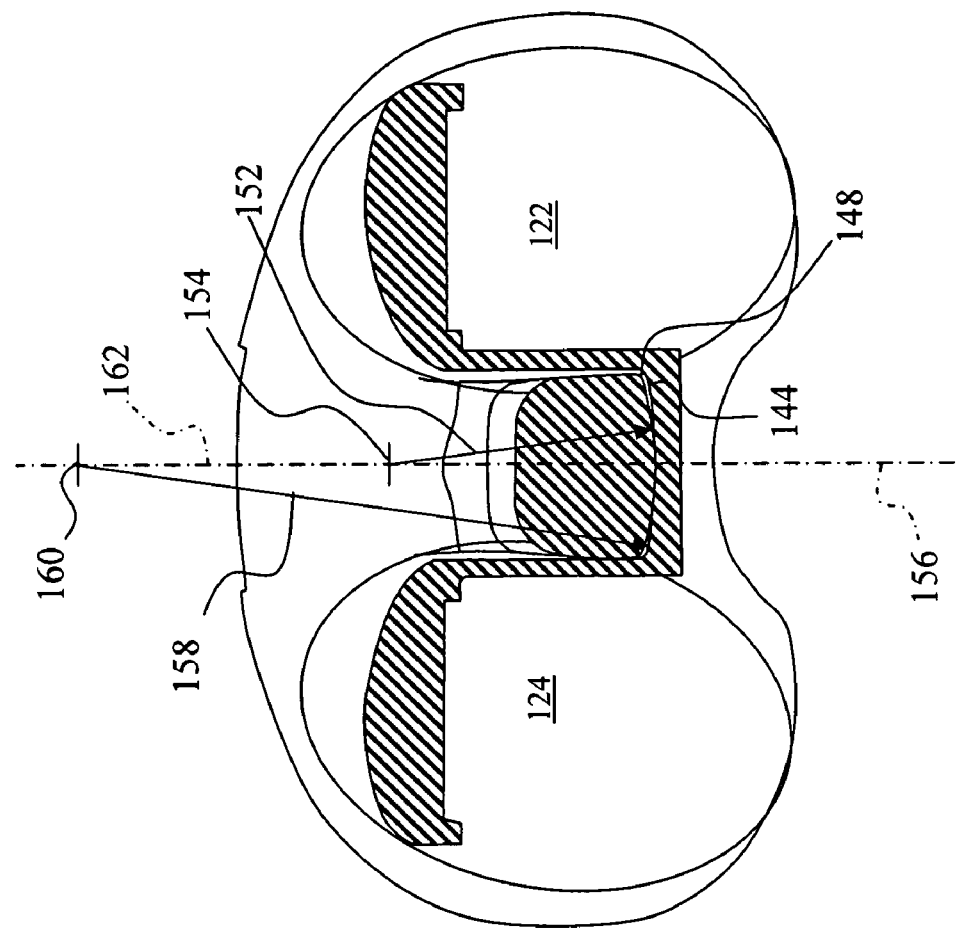
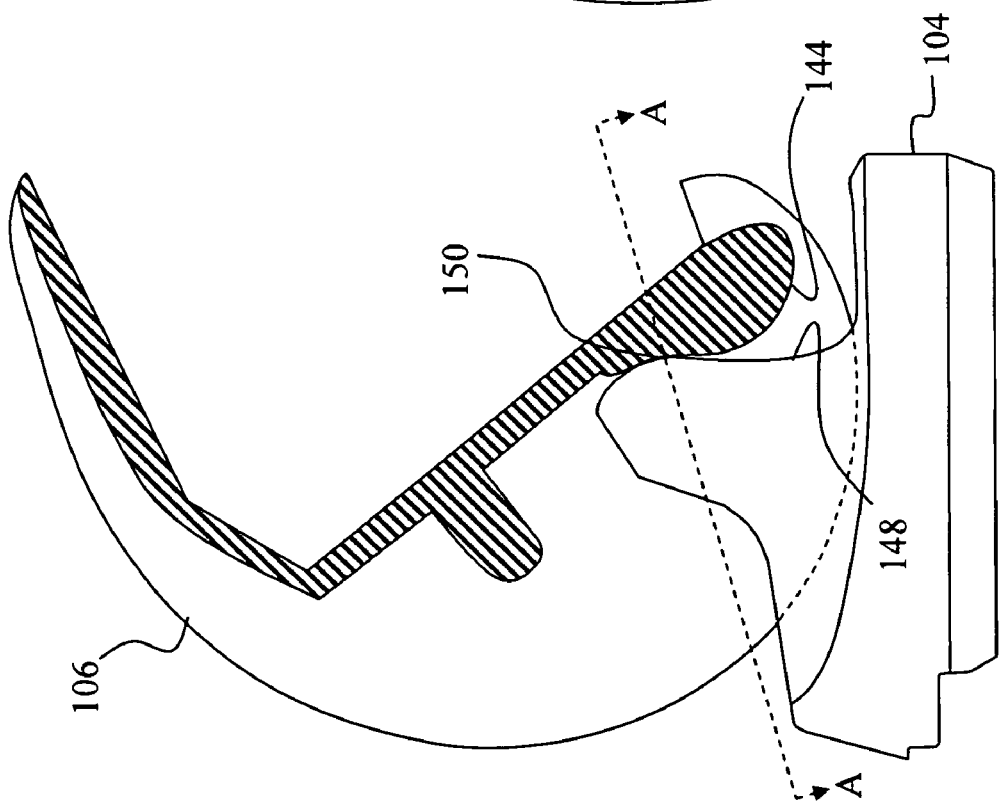
FIG. 8
FIG. 7

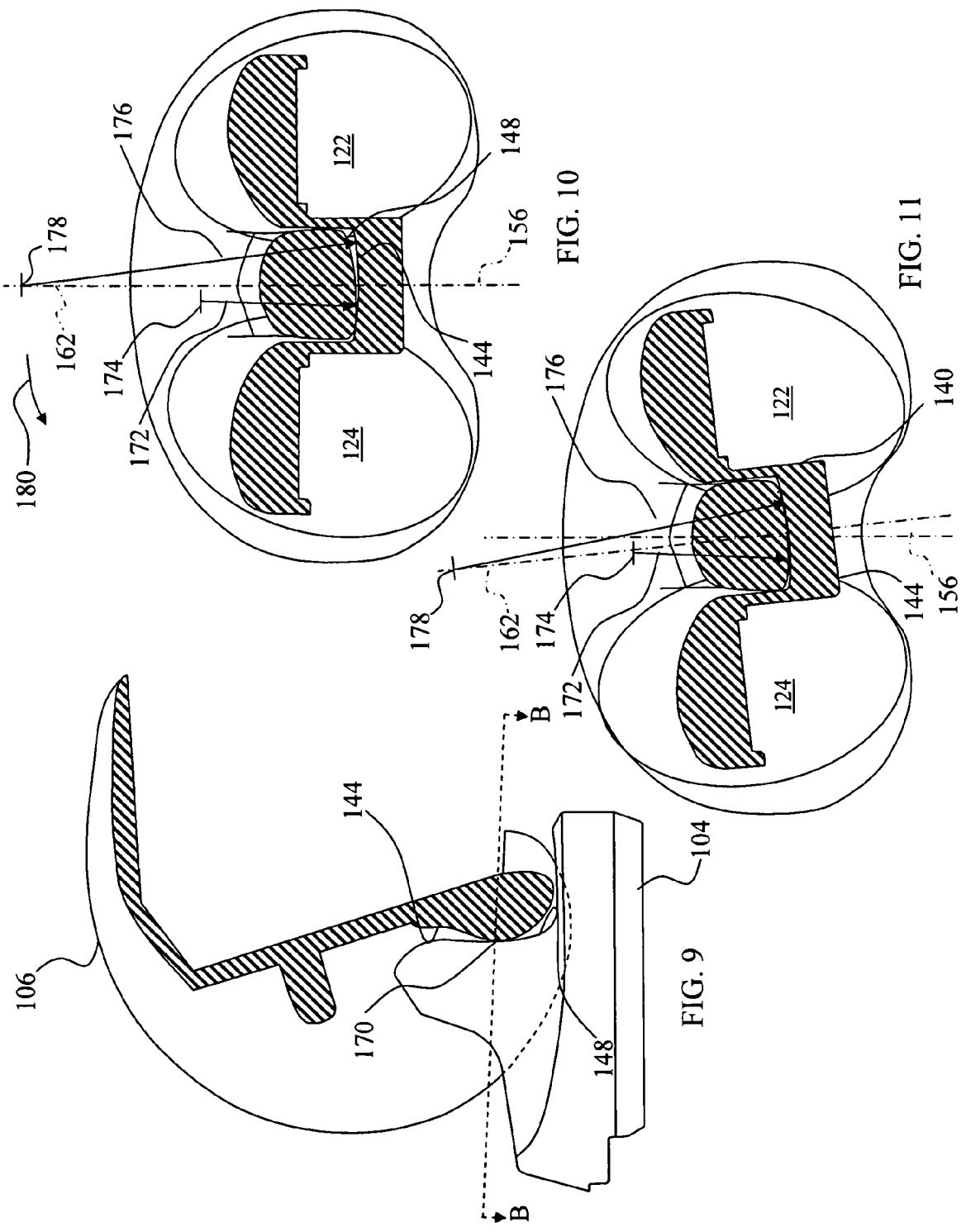

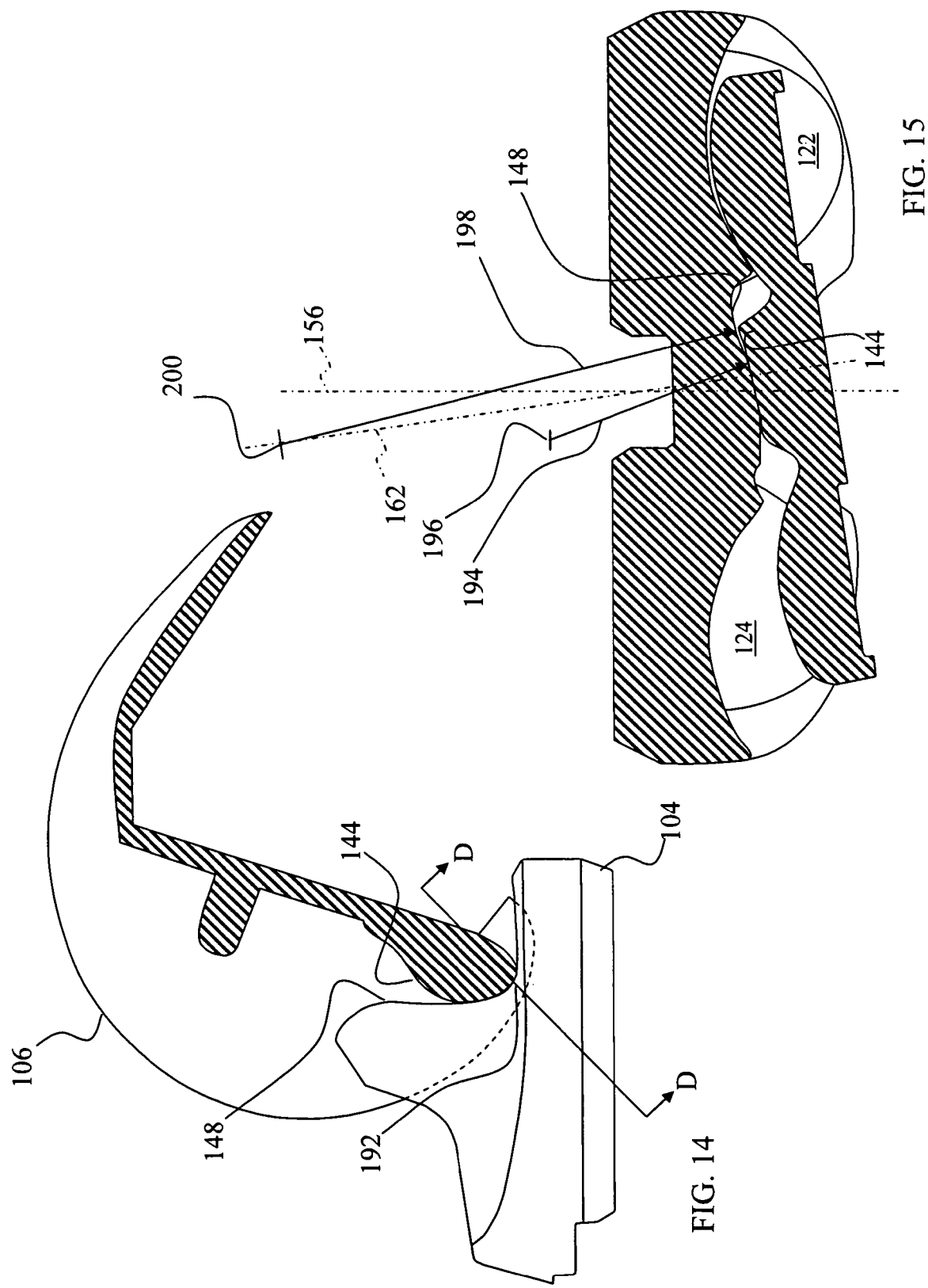

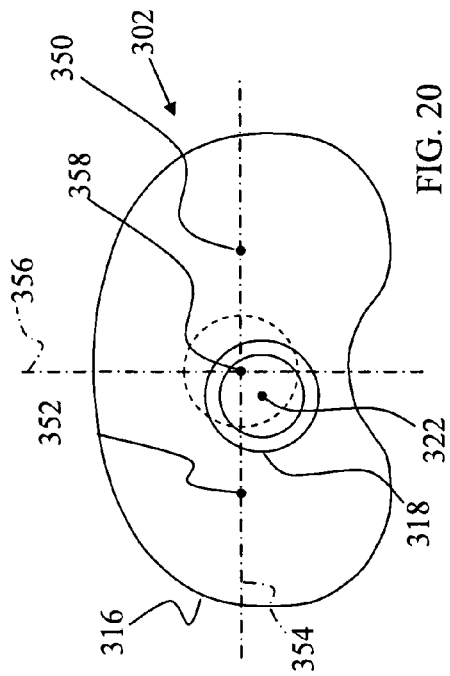
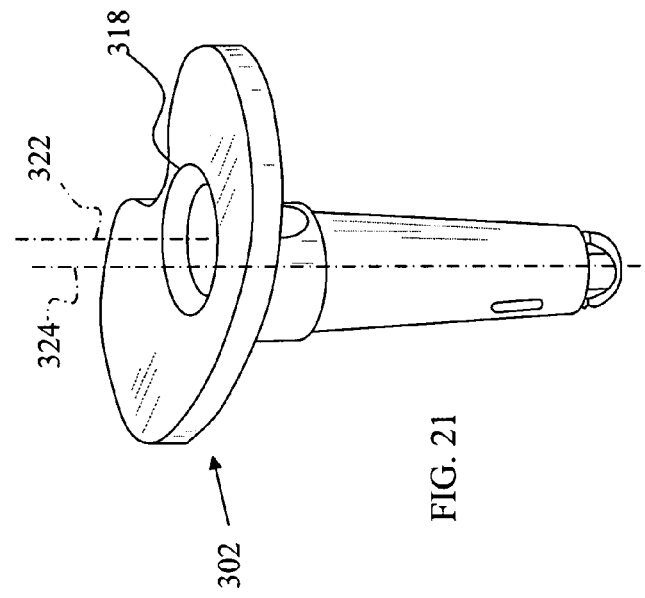
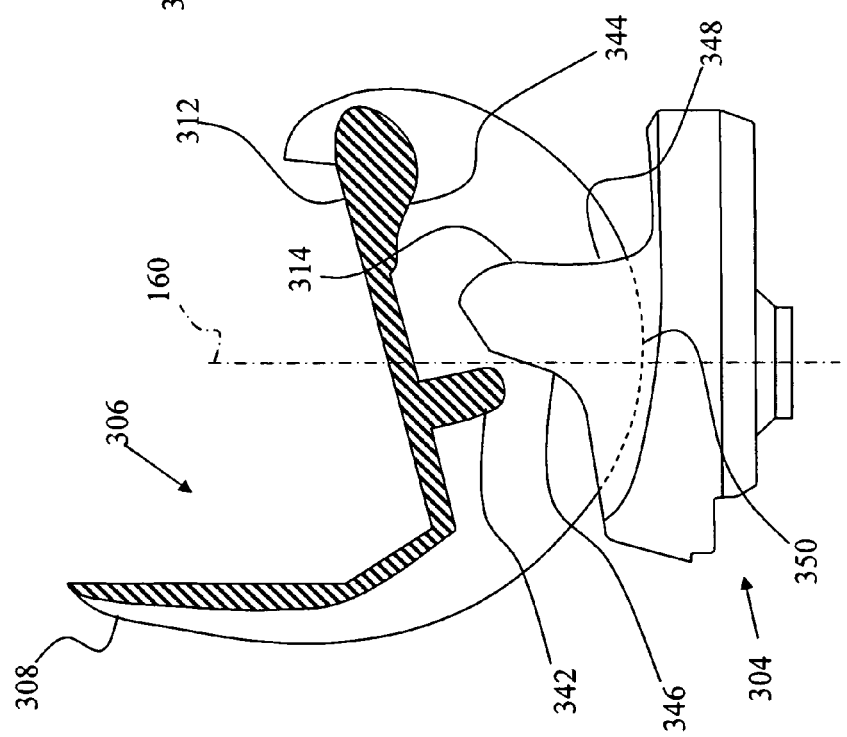

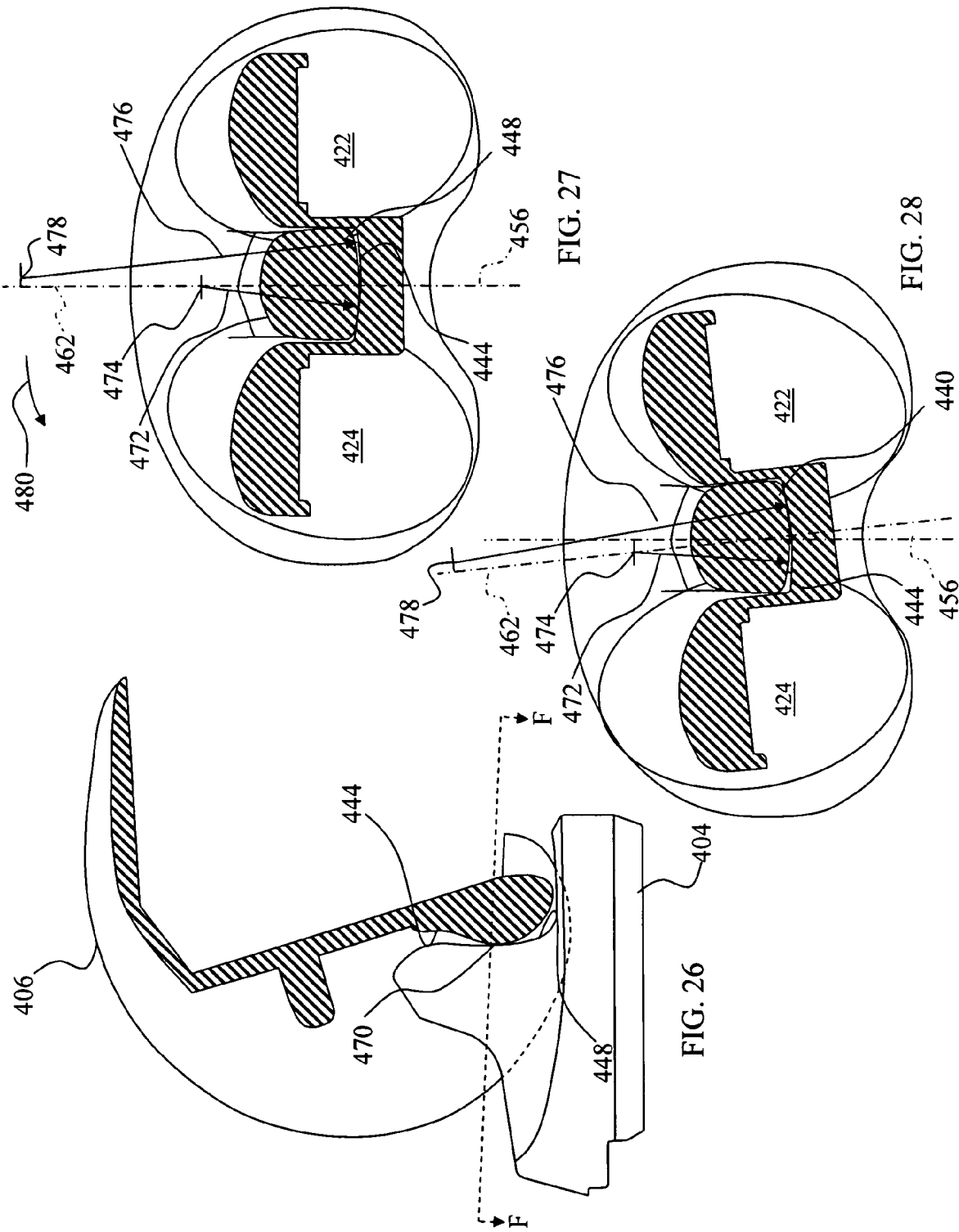

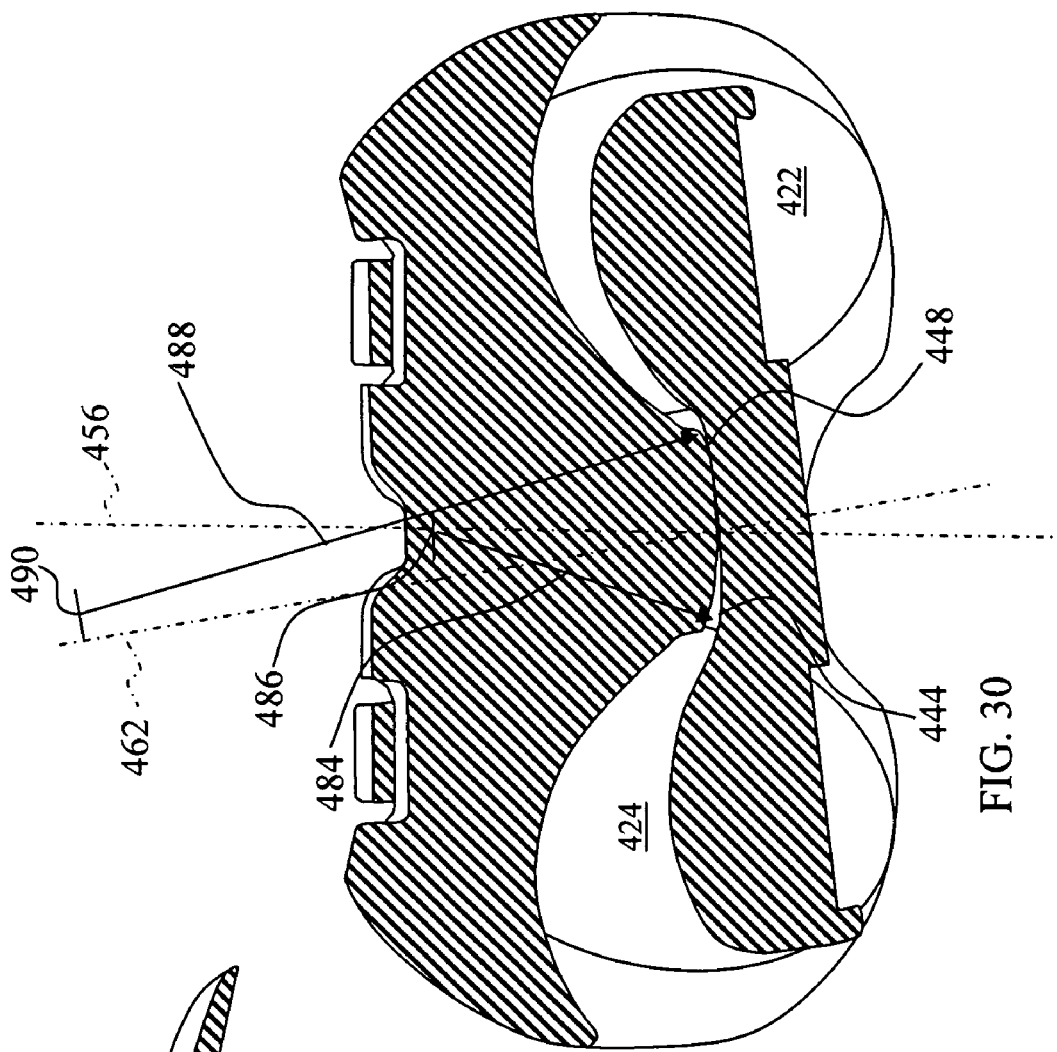
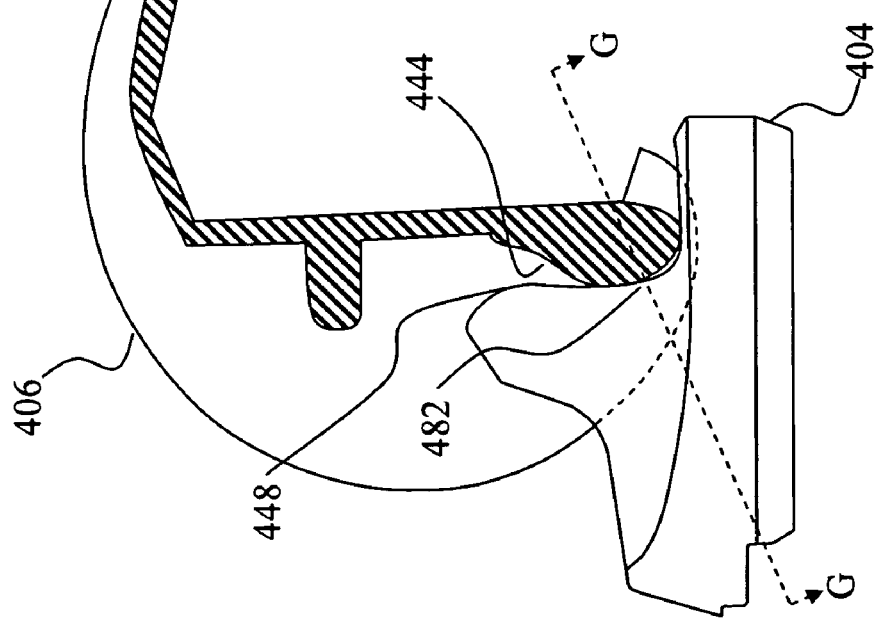
FIG. 30
FIG. 29

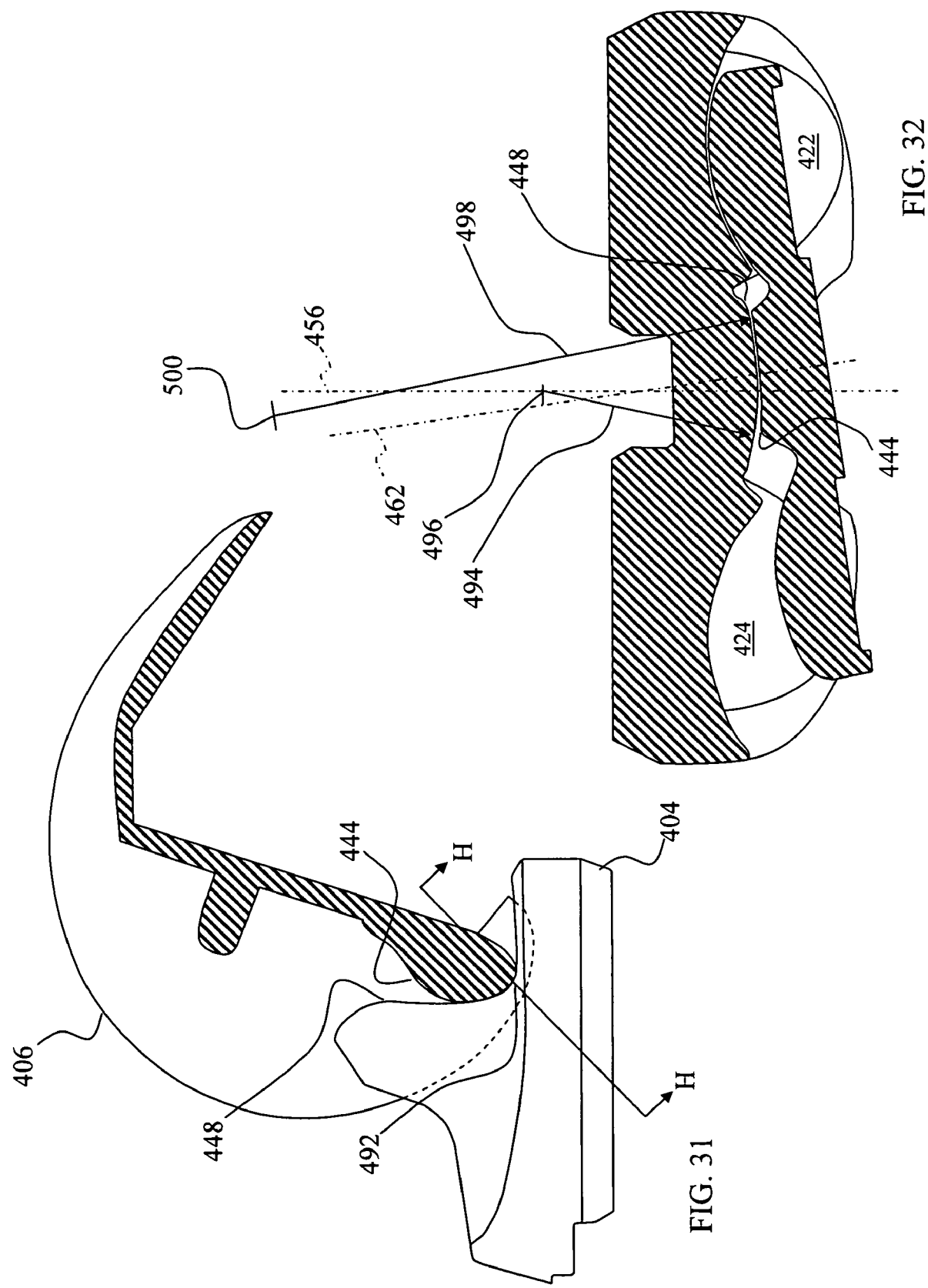

KNEE PROSTHESES WITH ENHANCED KINEMATICS

Cross-reference is made to U.S. Utility patent application Ser. No. 12/165,579 entitled "Orthopaedic Femoral Component Having Controlled Condylar Curvature" by John L. Williams et al., which was filed on Jun. 30, 2008; to U.S. Utility patent application Ser. No. 12/165,574 entitled "Posterior Cruciate-Retaining Orthopaedic Knee Prosthesis Having Controlled Condylar Curvature" by Christel M. Wagner, which was filed on Jun. 30, 2008; to U.S. Utility patent application Ser. No. 12/165,575 entitled "Posterior Stabilized Orthopaedic Knee Prosthesis Having Controlled Condylar Curvature" by Joseph G. Wyss, which was filed on Jun. 30, 2008; to U.S. Utility patent application Ser. No. 12/165,582 entitled "Posterior Stabilized Orthopaedic Prosthesis" by Joseph G. Wyss, which was filed on Jun. 30, 2008; to U.S. Utility patent application Ser. No. 12/174,507 entitled "Antero-Posterior Placement of Axis of Rotation for a Rotating Platform" by John L. Williams, et al., which was filed on Jul. 16, 2008; and to U.S. Provisional Patent Application Ser. No. 61/007,124 entitled "Orthopaedic Knee Prosthesis Having Controlled Condylar Curvature" by Joseph G. Wyss, which was filed on Jun. 30, 2008; the entirety of each of which is incorporated herein by reference. The principles of the present invention may be combined with features disclosed in those patent applications.

FIELD OF THE INVENTION

This invention relates generally to prostheses for human body joints, and, more particularly, to prostheses for knees.

BACKGROUND OF THE INVENTION

The knee joint provides six degrees of motion during dynamic activities. One such activity is deep flexion or bending of the knee joint. The six degrees of motion are effected by complex movements or kinematics of the bones and soft tissue in the knee joint. Most individuals are capable of controlling the complex movement of a knee joint without thought. The absence of conscious control belies the intricate interactions between a number of different components which are necessary to effect activities such as flexion and extension (when the leg is straightened) of a knee joint.

The knee joint includes the bone interface of the distal end of the femur and the proximal end of the tibia. The patella is positioned over the distal end of the femur and is positioned within the tendon of the long muscle (quadriceps) on the front of the thigh. This tendon inserts into the tibial tuberosity and the posterior surface of the patella is smooth and glides over the femur.

The femur is configured with two large eminences (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles. The complex interactions of the femur, the tibia and the patella are constrained by the geometry of the bony structures of the knee joint, the menisci, the muscular attachments via tendons, and the ligaments. The ligaments of the knee joint include the patellar ligament, the medial and lateral collateral ligaments, the anterior cruciate ligament (ACL) and the posterior cruciate ligament (PCL). The kinematics of the knee are further influenced by synovial fluid which lubricates the joint.

A number of studies have been directed to understanding the manner in which the various knee components interact as a knee joint moves through flexion. One such study was reported in an article by P. Johal, et al. entitled "Tibio-femoral movement in the living knee. A study of weight bearing and non-weight bearing knee kinematics using 'interventional' MRI, Journal of Biomechanics, Volume 38, Issue 2, February 2005, pages 269-276, which includes a FIG. 2 from which the data set forth in FIG. 1 as graph 10 has been derived. The graph 10 shows the locations of the medial and lateral condyle reference points of a native knee with respect to a tibia as the knee moves through flexion. The line 12 of the graph 10 indicates that the lateral condyle exhibits a constant anterior to posterior translation through deep flexion while the line 14 indicates that the medial condyle remains at about the same location on the tibial plateau until about 90 degrees of flexion. Beyond 90 degrees of flexion, the medial condyle exhibits anterior to posterior translation.

The medial and lateral condyle low (tangency) points are not the actual contact points between the condyles and the femoral plane. Rather, the points represent the lowest portion of the condyle that can be viewed using fluoroscopy. The actual contact point is generally at a location more posterior to the low (tangency) points. Nonetheless, the use of low (tangency) points provides a valid basis for comparison of the effect of changing design variables between components.

Damage or disease can deteriorate the bones, articular cartilage and ligaments of the knee. Such changes from the normal condition of the knee joint can ultimately affect the ability of the natural knee to function properly leading to pain and reduced range of motion. To ameliorate the conditions resulting from deterioration of the knee joint, prosthetic knees have been developed that are mounted to prepared ends of the femur and tibia.

While damage to soft tissue is avoided to the extent possible during knee replacement procedures, some tissue is necessarily sacrificed in replacing a portion of the femur and tibia. Thus, while the typical individual has learned how to coordinate the tensioning of the muscle fibers, ligaments and tendons to provide a smooth transition from a present positioning of the knee to a desired positioning without conscious thought, the sacrifice of tissue changes the physics of the knee. Accordingly, the configuration of soft tissue used to cause movement such as flexion and extension in a healthy knee, or even a pre-operative knee, no longer achieves the same results when the knee is replaced with a prosthesis. Additionally, the sacrifice of soft tissue results in reduced stability of the knee joint.

To compensate for the loss of stability that results from the damage to soft tissue, four general types of implants have been developed. In one approach, the PCL is retained. When the PCL is retained, patients frequently encounter an unnatural (paradoxical) anterior translation of the contact point between the lateral condyle of the femur and the tibia during deep knee-bend movements. Rather than rolling back or slipping as a knee moves through flexion, the femur slides anteriorly along the tibial platform. Paradoxical anterior translation is typically initiated between 30 and 40 degrees of flexion although it can commence at up to about 120 degrees of flexion. The resulting loss of joint stability can accelerate wear, cause a sensation of instability during certain activities of daily living, result in abnormal knee joint motion (kinematics), and/or result in a reduced dynamic moment arm to the quadriceps requiring increased force to control movement.

By way of example, FIG. 2 depicts a sagittal view of a typical prior art femoral component 20 which attempts to mimic the shape of a native knee. The femoral component 20 includes an extension region 22 which is generally anterior to the line 24 and a flexion region 26 which is posterior to the line 24. The extension region 22 is formed with a large radius of curvature ($R_c$) 28 while a small $R_c$ 30 is used in the posterior portion of the flexion region 26 in order to fit within the joint space while providing as much flexion as possible. Contemporaneously with the change of length of the radii of curvature, the origin of the radius of curvature changes from the origin 32 for the $R_c$ 28 to the origin 34 for the $R_c$ 30.

The results of a deep knee bending simulation using a typical prior art femoral component with condylar surfaces in the flexion area defined by a reduced radius of curvature are shown in the translation chart 40 of FIG. 3 which shows the position on the tibial component (y-axis) whereat the medial and lateral condyles contact the tibial component as the device is moved through flexion (x-axis). The simulation was conducted on a multibody dynamics program commercially available from Biomechanics Research Group, Inc. of San Clemente, Calif., under the name LifeMOD/KneeSIM. The model included tibio-femoral and patello-femoral contact, passive soft tissue, and active muscle elements.

The lines 42 and 44 in the chart 40 show the estimated low (tangency) points for the lateral condylar surface and the medial condylar surface, respectively. Both of the lines 42 and 44 initially track posteriorly (downwardly as viewed in FIG. 3) between 0 degrees and about 30 degrees of flexion. This indicates that the femoral component is rolling posteriorly on the tibial component as the flexion angle increases. Beyond about 30° of flexion, the estimated lateral condyle low (tangency) point line 42 drifts slightly anteriorly from about 5 mm translation while the estimated medial condylar low (tangency) point line 44 moves rapidly anteriorly. Movement of both surfaces in the anterior direction shows that paradoxical anterior translation is occurring beyond about 30 degrees. A comparison of the lines 42 and 44 beyond 30° of flexion with the lines 12 and 14 of FIG. 1 reveals a striking disparity in kinematics between the native knee and the replacement knee which mimics the geometry of the native knee.

Additionally, returning to FIG. 2, as the femoral component 20 is flexed such that contact with a tibial component (not shown) occurs along the condylar surface defined by the $R_c$ 28, the forces exerted by soft-tissues on the knee are coordinated to provide a smooth movement based, in part, upon the length of the $R_c$ 28 and the origin 32. As the femoral component 20 is moved through the angle at which the condylar surface transitions from the $R_c$ 28 to the $R_c$ 30, the knee may initially be controlled as if it will continue to move along the $R_c$ 28. As the femoral component 20 continues to move, the actual configuration of the knee diverges from the configuration that would be achieved if the surface in contact with the tibial component (not shown) was still defined by the $R_c$ 28. When the divergence is sensed, it is believed that the soft-tissue forces are rapidly re-configured to a configuration appropriate for movement along the surface defined by the $R_c$ 30 with the origin 34. This sudden change in configuration, which is not believed to occur with a native knee, contributes to the sense of instability.

Furthermore, Andriacchi, T. P., *The Effect of Knee Kinematics, Gait and Wear on the Short and Long-Term Outcomes of Primary Total Knee Replacement*, NIH Consensus Development Conference on Total Knee Replacement, pages 61-62, (Dec. 8-10, 2003) reports that in a native knee, flexion between 0 and 120 degrees is accompanied by approximately 10 degrees of external rotation of the femur with respect to the tibia while an additional 20 degrees of external rotation is required for flexion from 120 degrees to 150 degrees. Thus, an initial ratio of about 0.008 degrees of external rotation per degree of flexion is exhibited between 0 degrees and 120 degrees of flexion which increases to a ratio of 0.67 degrees of external rotation per degree of flexion between 120 degrees and 150 degrees of flexion. This rotation allows the knee to move into deep flexion.

The reported external rotation of the native knee is supported by the data in FIG. 1. Specifically, between about 9 degrees and 90 degrees of flexion, the slope of the line 12 is constantly downward indicating that the lowest point of the lateral condylar surface is continuously tracking posteriorly. The line 14, however, is moving anteriorly from about 9 degrees of flexion through 90 degrees of flexion. Thus, assuming this difference to be solely due to external rotation, the femoral component is externally rotating as the knee moved from about 9 degrees of flexion to about 90 degrees of flexion. Beyond 90 degrees of flexion, the lines 12 and 14 show that both condylar surfaces are moving posteriorly. The lateral condylar surface, however, is moving more rapidly in the posterior direction. Accordingly, the gap between the lines 12 and 14 continues to expand beyond 90 degrees, indicating that additional external rotation of the knee is occurring.

FIG. 4 shows the internal rotation of the tibia with respect to the femur (which from a modeling perspective is the same as external rotation of the femur with respect to the tibia, both of which are identified herein as "$\phi_{i-e}$") during the testing that provided the results of FIG. 3. The graph 50 includes a line 52 which shows that as the tested component was manipulated to 130 degrees of flexion, the $\phi_{i-e}$ reached a maximum of about seven degrees. Between about 0 degrees of flexion and 20 degrees of flexion, the $\phi_{i-e}$ varies from 1 degree to zero degrees for a change rate of −0.05 degrees of internal rotation per degree of flexion. Between about 20 degrees of flexion and 50 degrees of flexion, the internal rotation varies from 0 degrees to 1 degree for a change rate of 0.03 degrees of internal rotation per degree of flexion. Between about 50 degrees and 130 degrees, the graph 50 exhibits a nearly linear increase in internal rotation from about 1 degree to about 7 degrees for a change rate of 0.075 degrees of internal rotation per degree of flexion. Accordingly, the $\phi_{i-e}$ of a knee joint incorporating the prior art femoral component differs significantly from the $\phi_{i-e}$ of a native knee.

Various attempts have been made to provide kinematics more akin to those of the native knee. For example, the problem of paradoxical anterior translation in one type of implant is addressed by sacrificing the PCL and relying upon articular geometry to provide stability. In another type of implant, the implant is constrained. That is, an actual linkage is used between the femoral and tibial components. In another type of implant, the PCL is replaced with a cam on the femoral component and a post on the tibial component. While the foregoing approaches have some effectiveness with respect to paradoxical anterior translation, they do not provide other kinematics exhibited by a native knee.

What is needed is a knee prosthesis that more closely reproduces the inherent stability and kinematics of a native knee such as by managing rotation and rollback.

SUMMARY

The present invention is a knee replacement system. In one embodiment, a prosthetic joint includes a proximal tibial camming portion (i) extending from a lateral portion of a posterior tibial cam to a medial portion of the posterior tibial cam, (ii) defined by a first radius of curvature in a first mediolateral plane, and (iii) having a first origin, a distal tibial camming portion (i) extending from the lateral portion of the posterior tibial cam to the medial portion of the posterior tibial cam, (ii) defined by a second radius of curvature in a second medio-lateral plane, and (iii) having a second origin, an anterior femoral camming portion (i) extending from a lateral portion of a posterior femoral cam to a medial portion of the posterior femoral cam, (ii) defined by a third radius of curvature in the first medio-lateral plane, and (iii) having a third origin, a posterior femoral camming portion extending from the lateral portion of the posterior femoral cam to the medial portion of the posterior femoral cam and defined by a fourth radius of curvature in the second medio-lateral plane and having a fourth origin, wherein the second origin is closer to the lateral tibial portion than the first origin, or the fourth origin is closer to the medial femoral portion than the third origin.

In a further embodiment, a knee prosthesis includes a tibial cam including a posterior camming surface defined by a plurality of radii of curvature, each of the plurality of tibial radii of curvature (i) located in an associated one of a plurality of medio-lateral planes perpendicular to the camming surface, and (ii) having an origin spaced apart from each of the origins of the other of the plurality of tibial radii of curvature in the medio-lateral direction, and a posterior femoral cam including a distal camming surface defined by a plurality of radii of curvature, each of the plurality of femoral radii of curvature located in an associated one of a plurality of medio-lateral planes perpendicular to the camming surface.

In another embodiment, a knee prosthesis includes a tibial cam including a posterior camming surface defined by a plurality of radii of curvature, each of the plurality of tibial radii of curvature located in an associated one of a plurality of medio-lateral planes perpendicular to the camming surface, and a posterior femoral cam including a distal camming surface defined by a plurality of radii of curvature, each of the plurality of femoral radii of curvature (i) located in an associated one of a plurality of medio-lateral planes perpendicular to the camming surface, and (ii) having an origin spaced apart from each of the origins of the other of the plurality of femoral radii of curvature in the medio-lateral direction.

The above-described features and advantages, as well as others, will become more readily apparent to those of ordinary skill in the art by reference to the following detailed description and accompanying drawings.

BRIEF DESCRIPTION OF THE DRAWINGS

FIG. 7 depicts a sagittal cross sectional view of the femoral component of FIG. 5 and a sagittal plan view of the tibial bearing insert of FIG. 5 showing the contact region between the camming surfaces of the femoral component and the tibial bearing insert with the femoral component positioned at about 70 degrees of flexion on the tibial bearing insert;

FIG. 8 depicts a medio-lateral cross sectional view of the configuration of FIG. 7 taken along the line A-A of FIG. 7 showing the origins of the radius of curvature of the camming surfaces of the femoral component and the tibial bearing insert to be located on the centerlines of the respective component;

FIG. 9 depicts a sagittal cross sectional view of the femoral component of FIG. 5 and a sagittal plan view of the tibial bearing insert of FIG. 5 showing the contact region between the camming surfaces of the femoral component and the tibial bearing insert with the femoral component positioned at about 90 degrees of flexion on the tibial bearing insert;

FIG. 10 depicts a medio-lateral cross sectional view of the configuration of FIG. 9 taken along the line B-B of FIG. 9 with the centerlines of the femoral and tibial components aligned showing the origin of the radius of curvature of the femoral component camming surface to be located on the centerline of the femoral component and the origin of the radius of curvature of the tibial bearing insert camming surface to be located laterally of the centerline of the tibial bearing insert;

FIG. 11 depicts a medio-lateral cross sectional view of the configuration of FIG. 9 taken along the line B-B of FIG. 9 showing the rotation of the femoral component that has occurred because of increased rollback of the lateral condyle element resulting from locating the origin of the radius of curvature of the femoral component on the centerline of the femoral component and locating the origin of the radius of curvature of the tibial bearing insert camming surface laterally of the centerline of the tibial bearing insert;

FIG. 14 depicts a sagittal cross sectional view of the femoral component of FIG. 5 and a sagittal plan view of the tibial bearing insert of FIG. 5 showing the contact region between the camming surfaces of the femoral component and the tibial bearing insert with the femoral component positioned at about 130 degrees of flexion on the tibial bearing insert;

FIG. 15 depicts a medio-lateral cross sectional view of the configuration of FIG. 14 taken along the line D-D of FIG. 14 showing the rotation of the femoral component that has occurred because of increased rollback of the lateral condyle element resulting from locating the origin of the radius of curvature of the femoral component on the centerline of the femoral component and locating the origin of the radius of curvature of the tibial bearing insert camming surface laterally of the centerline of the tibial bearing insert;

FIG. 19 depicts a sagittal cross sectional view of the femoral component of FIG. 18 and a sagittal plan view of the tibial bearing insert of FIG. 18 showing the camming surfaces of the femoral component and the tibial bearing insert with the femoral component positioned in extension on the tibial bearing insert;

FIG. 20 depicts a top plan view of the dwell axis and the centerline of the tibial insert of the knee prosthesis of FIG. 18 projected onto the articulating surface of the tibial tray of the knee prosthesis of FIG. 18;

FIG. 21 depicts a perspective view of the tibial tray of the knee prosthesis of FIG. 18 with the coupler member defining an axis of rotation for the tibial bearing insert;

FIG. 26 depicts a sagittal cross sectional view of the femoral component of FIG. 24 and a sagittal plan view of the tibial bearing insert of FIG. 24 showing the contact region between the camming surfaces of the femoral component and the tibial bearing insert with the femoral component positioned at about 90 degrees of flexion on the tibial bearing insert;

FIG. 27 depicts a medio-lateral cross sectional view of the configuration of FIG. 26 taken along the line F-F of FIG. 26 with the centerlines of the femoral and tibial components aligned showing the origin of the radius of curvature of the femoral component camming surface to be located medially of the centerline of the femoral component and the origin of the radius of curvature of the tibial bearing insert camming surface to be located on the centerline of the tibial bearing insert;

FIG. 28 depicts a medio-lateral cross sectional view of the configuration of FIG. 26 taken along the line F-F of FIG. 26 showing the rotation of the femoral component that has occurred because of increased rollback of the lateral condyle element resulting from locating the origin of the radius of curvature of the femoral component medially of the centerline of the femoral component and locating the origin of the radius of curvature of the tibial bearing insert camming surface on the centerline of the tibial bearing insert;

FIG. 29 depicts a sagittal cross sectional view of the femoral component of FIG. 24 and a sagittal plan view of the tibial bearing insert of FIG. 24 showing the contact region between the camming surfaces of the femoral component and the tibial bearing insert with the femoral component positioned at about 110 degrees of flexion on the tibial bearing insert;

FIG. 30 depicts a medio-lateral cross sectional view of the configuration of FIG. 29 taken along the line G-G of FIG. 29 showing the rotation of the femoral component that has occurred because of increased rollback of the lateral condyle element resulting from locating the origin of the radius of curvature of the femoral component medially of the centerline of the femoral component and locating the origin of the radius of curvature of the tibial bearing insert camming surface on the centerline of the tibial bearing insert;

FIG. 31 depicts a sagittal cross sectional view of the femoral component of FIG. 24 and a sagittal plan view of the tibial bearing insert of FIG. 24 showing the contact region between the camming surfaces of the femoral component and the tibial bearing insert with the femoral component positioned at about 130 degrees of flexion on the tibial bearing insert; and FIG. 32 depicts a medio-lateral cross sectional view of the configuration of FIG. 31 taken along the line H-H of FIG. 31 showing the rotation of the femoral component that has occurred because of increased rollback of the lateral condyle element resulting from locating the origin of the radius of curvature of the femoral component medially of the centerline of the femoral component and locating the origin of the radius of curvature of the tibial bearing insert camming surface on the centerline of the tibial bearing insert.

DETAILED DESCRIPTION

Figure 1:
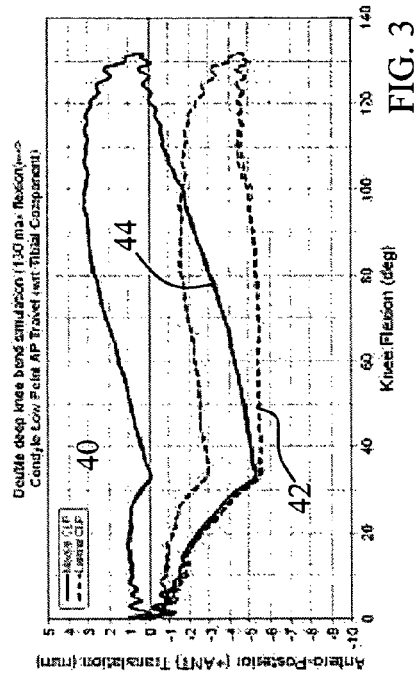
FIG. 1 shows a graph of the reference point locations of the medial and lateral condyle on a tibial component for a native knee during deep knee bending.
Figure 2:
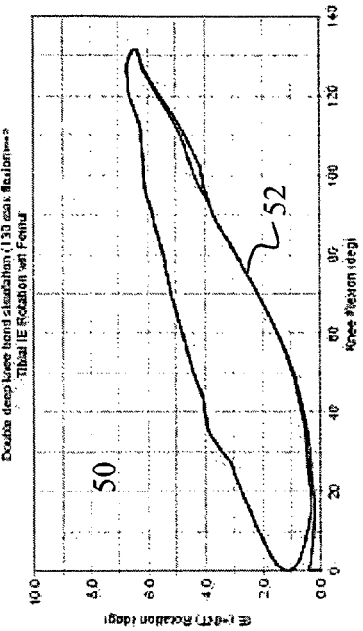
FIG. 2 depicts a sagittal view of a prior art femoral component of a prosthesis.
Figure 3:
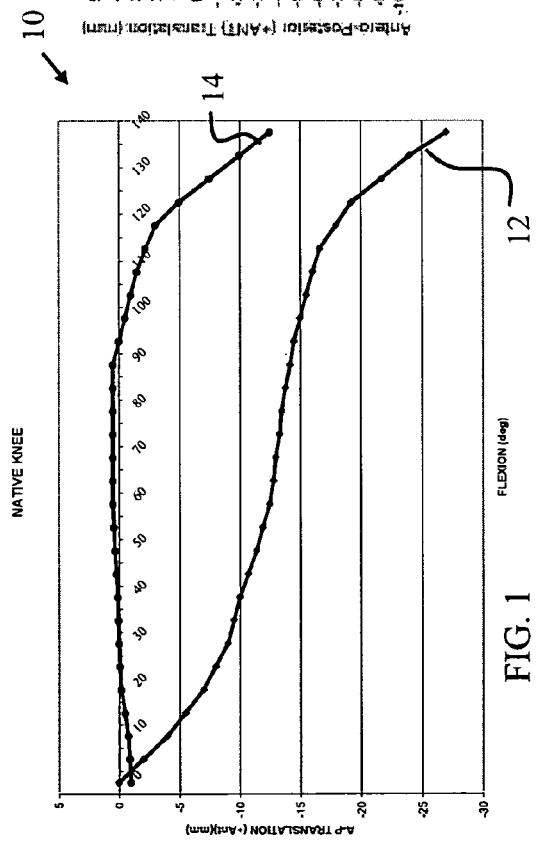
FIG. 3 shows the results of a simulation in the form of a graph of the estimated low (tangency) point locations of the medial and lateral condyles of a femoral component on a tibial component.
Figure 4:
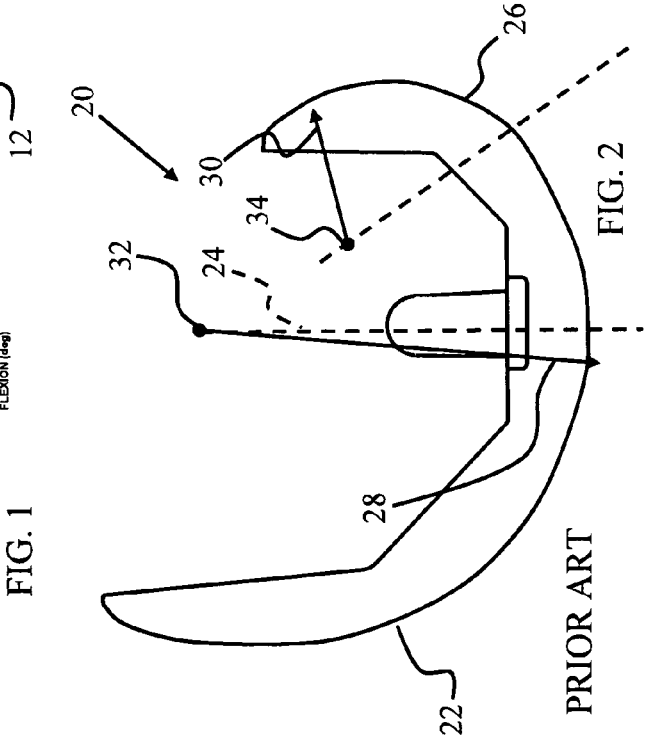
FIG. 4 shows the internal rotation of the tibial component with respect to the femoral component for the simulation of FIG. 3.
Figure 5:
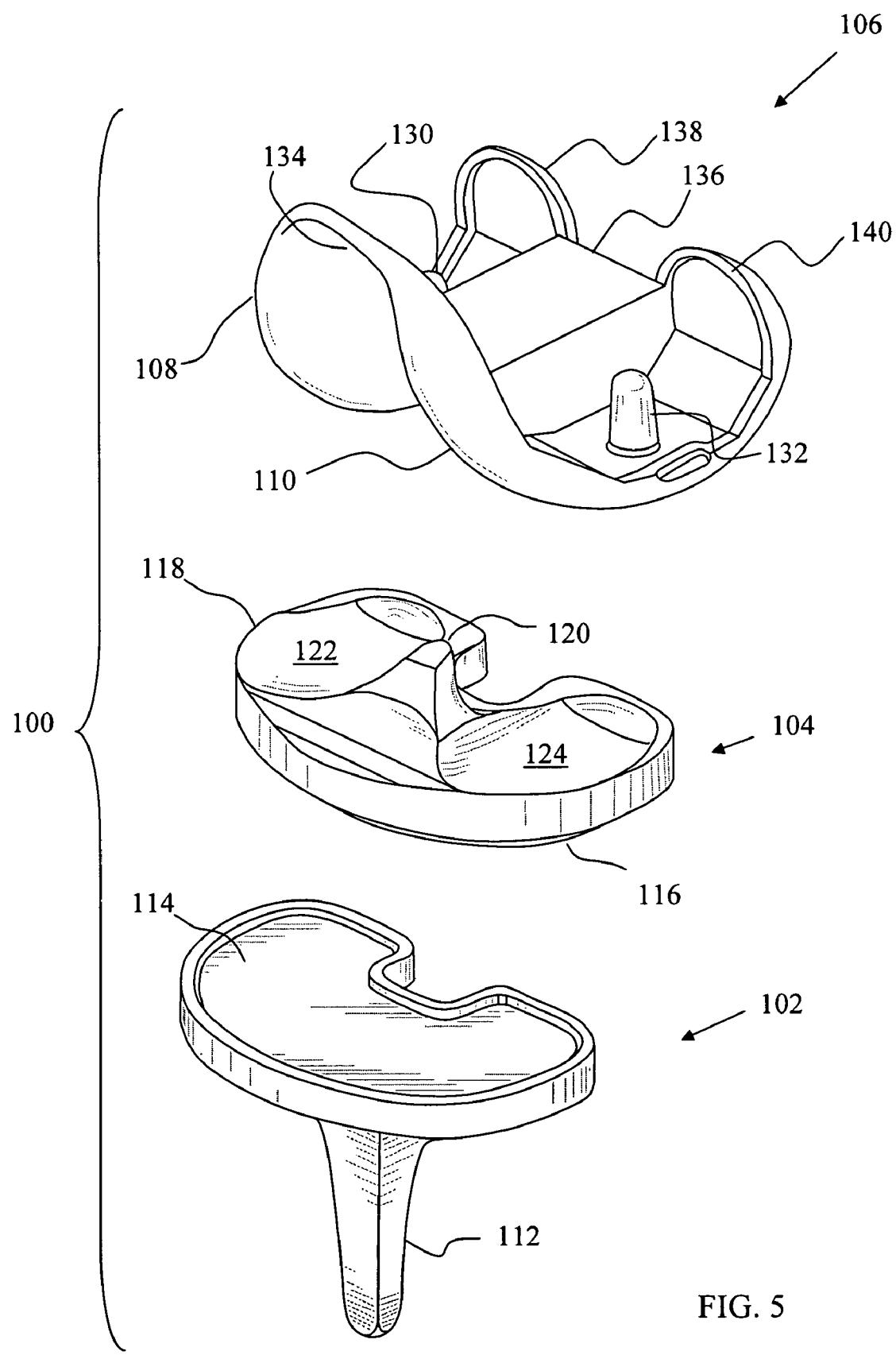
FIG. 5 depicts an exploded perspective view of a knee prosthesis including a tibial component and a femoral component in accordance with principles of the invention.

FIG. 5 depicts a knee replacement system 100. The knee replacement system 100 includes a tibial tray 102, a tibial bearing insert 104 and a femoral component 106 having two femoral condyle elements 108 and 110. The tibial tray 102 includes an inferior stem 112 for attaching the tibial tray 102 to the tibia of a patient and a superior plateau 114 for receiving the tibial bearing insert 104. The tibial bearing insert 104 in this embodiment is fixed and includes an inferior tibial tray contacting surface 116 and a superior tibial bearing surface 118 configured to articulate with the femoral condyle elements 108 and 110. A spine 120 separates the superior tibial bearing surface 118 into a bearing surface 122 and a bearing surface 124.

The femoral component 106 includes two pegs 130 and 132 which are used to attach the femoral component 106 to the femur of a patient. A trochlear groove 134 is formed between the femoral condyle elements 108 and 110. The trochlear groove 134 provides an articulation surface for a patellar component (not shown). A cam compartment 136 is located between posterior portions 138 and 140 of the femoral condyle elements 108 and 110, respectively.

The femoral condyle elements 108 and 110, in this embodiment, are symmetrical. The femoral component 106 and the tibial bearing insert 104 in this embodiment, however, are configured only for use in a left knee. More specifically, the femoral component 106 and the tibial bearing insert 104 are configured to simulate the motion of a natural left knee when implanted in a patient. The configuration is discussed with further reference to FIG. 6.

Figure 6:
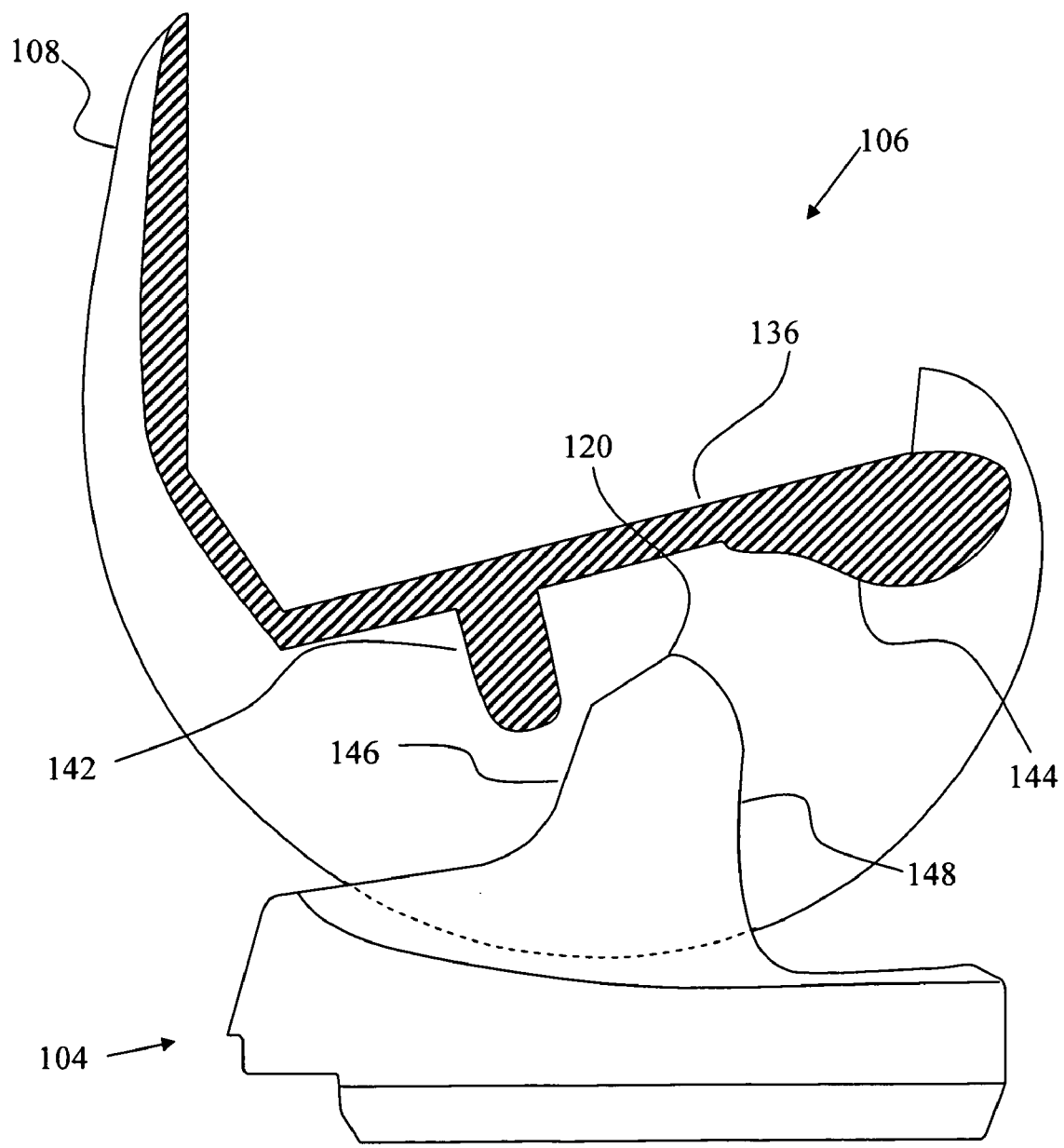
FIG. 6 depicts a sagittal cross sectional view of the femoral component of FIG. 5 and a sagittal plan view of the tibial bearing insert of FIG. 5 showing the camming surfaces of the femoral component and the tibial bearing insert with the femoral component positioned in extension on the tibial bearing insert.

FIG. 6 depicts a cross sectional view of the femoral component 106 taken through the cam compartment 136 and a side plan view of the tibial bearing insert 104. An anterior cam 142 and a posterior cam 144 are located within the cam compartment 136. The spine 120 includes an anterior camming portion 146 and a posterior camming portion 148. The anterior cam 142 is configured with the anterior camming portion 146 to preclude undesired posterior slippage when the femoral component 106 is positioned on the tibial bearing insert 104 in extension as shown in FIG. 6. The actual shapes of the anterior cam 142 and the anterior camming portion 146 may be modified from the shape depicted in FIG. 6.

The shape and position of the posterior cam 144 and the shape and position of the posterior camming portion 148 are selected such that the posterior cam 144 and the posterior camming portion 148 are not in contact when the femoral component 106 is positioned on the tibial bearing insert 104 in extension. As the femoral component 106 is rotated into flexion, rollback of the femoral component 106 on the bearing surfaces 122 and 124 is controlled by the configuration of the femoral component 106 and the bearing surfaces 122 and 124. When flexion reaches about 70 degrees, however, the posterior cam 144 and the posterior camming portion 148 produce an effect on the rollback.

With reference to FIG. 7, the femoral component 106 is depicted rotated to about 70 degrees of flexion on the tibial bearing insert 104. At this rotation, the posterior cam 144 and the posterior camming portion 148 are in contact at the contact region 150. FIG. 8 depicts the shape of the posterior camming portion 148 and the shape of the posterior cam 144 at the contact region 150 taken along the line A-A of FIG. 7 which extends from a medial portion of the camming portion 148 and the posterior cam 144 to a lateral portion of the camming portion 148 and the posterior cam 144 in a medio-lateral plane.

The posterior camming portion 148 is formed on a radius of curvature $(R_c)$ 152 having an origin 154 on the centerline 156 of the tibial bearing insert 104. In one embodiment, the $R_c$ 152 may be about 20 millimeters. The posterior cam 144 is formed on a radius of curvature $(R_c)$ 158 having an origin 160 on the centerline 162 of the femoral component 106. In one embodiment, the $R_c$ 158 may be about 40 millimeters.

The centerline 156, also referred to herein as the "centerline of the tibial component" is defined as (i) the straight line extending between the origin of the radius of curvature of the posterior cam 144 and the origin of the radius of curvature of the posterior camming portion 148, (ii) wherein the foregoing origins are the origins for the co-planar radii of curvature of the posterior cam 144 and the posterior camming portion 148 (iii) at a location where the posterior cam 144 and the posterior camming portion 148 are in contact (iv) when the posterior cam 144 and the posterior camming portion 148 first come into contact during rollback. In the embodiment of FIG. 7, the centerline 156 is thus defined by the origin 160 and the origin 154. The centerline 156 is fixed with respect to the tibial bearing insert 104, that is, if the tibial bearing insert 104 moves or rotates from the orientation depicted in FIG. 8, the centerline 156 moves or rotates as well.

Similarly, the centerline 162, also referred to herein as the "centerline of the femoral component," is defined as (i) the straight line extending between the origin of the radius of curvature of the posterior cam 144 and the origin of the radius of curvature of the posterior camming portion 148, (ii) wherein the foregoing origins are the origins for the co-planar radii of curvature of the posterior cam 144 and the posterior camming portion 148 (iii) in at a location where the posterior cam 144 and the posterior camming portion 148 are in contact (iv) when the posterior cam 144 and the posterior camming portion 148 first come into contact during rollback. In the embodiment of FIG. 7, the centerline 162 is thus defined by the origin 160 and the origin 154. The centerline 162 is fixed with respect to the femoral component 106, that is, if the femoral component 106 moves or rotates from the orientation depicted in FIG. 8, the centerline 162 moves or rotates as well.

At about 70 degrees of flexion, the centerline 156 of the tibial bearing insert 104 and the centerline 162 of the femoral component 106 are substantially aligned. Thus, the origin 154 and the origin 160 are substantially aligned. Accordingly, the predominant effect of the contact between the posterior cam 144 and the posterior camming portion 148 is the prevention of anterior movement of the femoral component 106 on the tibial bearing insert 104.

Continued rotation of the femoral component 106 to about 90 degrees of flexion on the tibial bearing insert 104 results in the configuration of FIG. 9. At this rotation, the posterior cam 144 and the posterior camming portion 148 are in contact at the contact region 170. FIG. 10 depicts the shape of the posterior camming portion 148 and the shape of the posterior cam 144 at the contact region 170 taken along the line B-B of FIG. 9.

In FIG. 10, the $R_c$ 172 of the posterior camming portion 148 has the same length as the $R_c$ 152 of FIG. 8. The length of the $R_c$ 172 may be modified to be longer or shorter than the $R_c$ 152 if desired. The $R_c$ 172, however, has an origin 174 which is positioned to the lateral side of the centerline 156. In one embodiment, the origin 174 is located 1.5 millimeters to the lateral side of the centerline 156. Additionally, the posterior cam 144 is formed with an $R_c$ 176 which in this embodiment is of the same length as the $R_c$ 158, although a longer or shorter length than the $R_c$ 158 may be selected, and the origin 178 of the $R_c$ 176 is positioned on the centerline 162. Accordingly, the shape of the posterior camming portion 148 and the posterior cam 144 cause a rotational force in the direction of the arrow 180. The lateral condyle, femoral condyle element 110 in this embodiment, is thus forced to move posteriorly at a rate greater than the medial condyle (femoral condyle element 108).

The result of the forces acting upon the femoral component 106 is rotation of the femoral component 106 with respect to the tibial bearing insert 104 as shown in FIG. 11. In FIG. 11, the centerline 162 has rotated in a counterclockwise direction from the centerline 156. Additionally, opposing faces of the posterior camming portion 148 and the posterior cam 144, in contrast to the configuration shown in FIG. 10, are more aligned with each other.

The movement of the origins of the $R_c$ for the posterior camming portion 148 and the posterior cam 144 is done incrementally along the contact surfaces of the posterior camming portion 148 between the contact region 150 and the contact region 170. This provides a smooth rotational movement of the femoral component 106 on the tibial bearing insert 104 from the alignment of FIG. 8 to the alignment of FIG. 11. The precise amount of rotation and rollback may be adjusted by modifying the offset of the origins.

Figure 13:
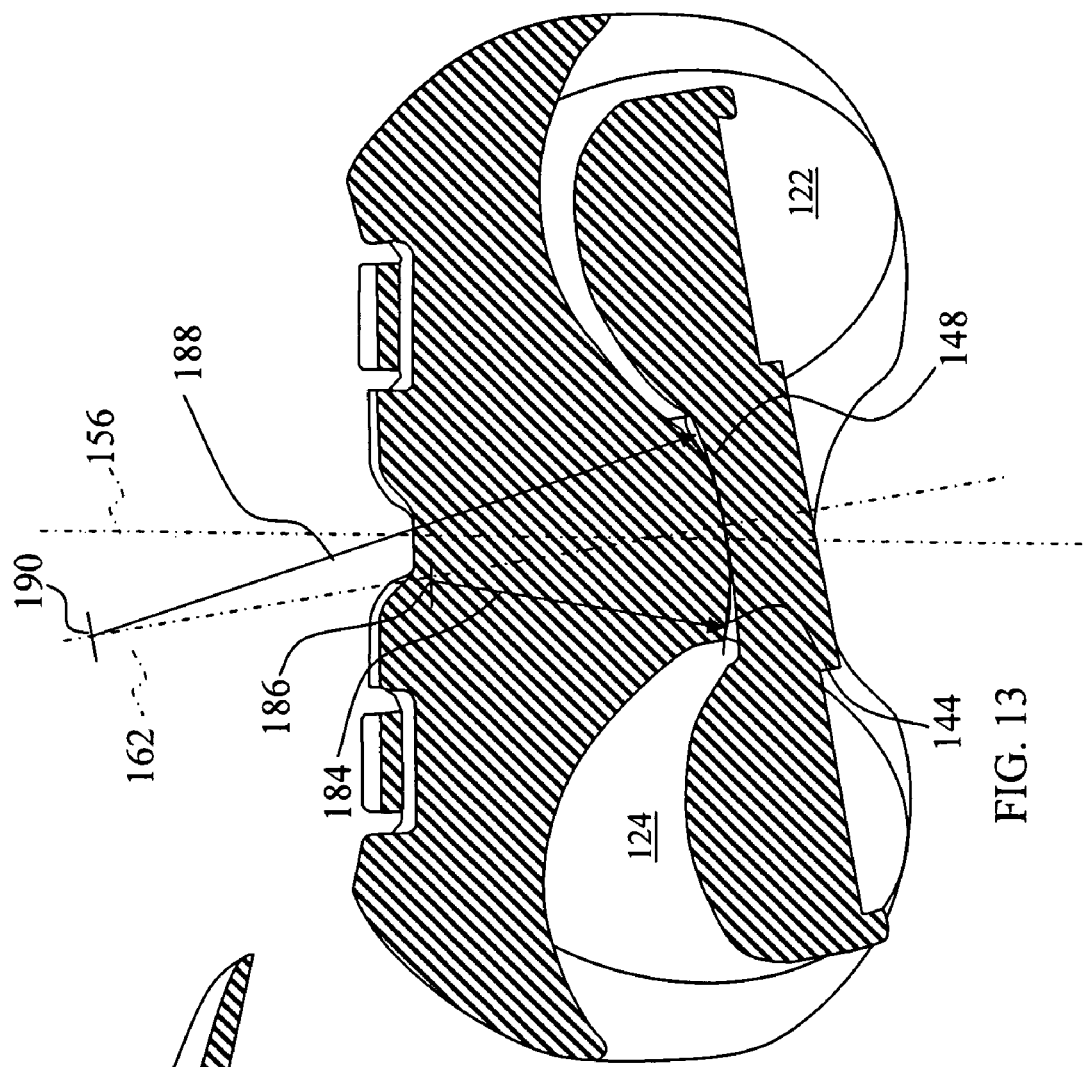
FIG. 13 depicts a medio-lateral cross sectional view of the configuration of FIG. 12 taken along the line C-C of FIG. 12 showing the rotation of the femoral component that has occurred because of increased rollback of the lateral condyle element resulting from locating the origin of the radius of curvature of the femoral component on the centerline of the femoral component and locating the origin of the radius of curvature of the tibial bearing insert camming surface laterally of the centerline of the tibial bearing insert.
Figure 12:
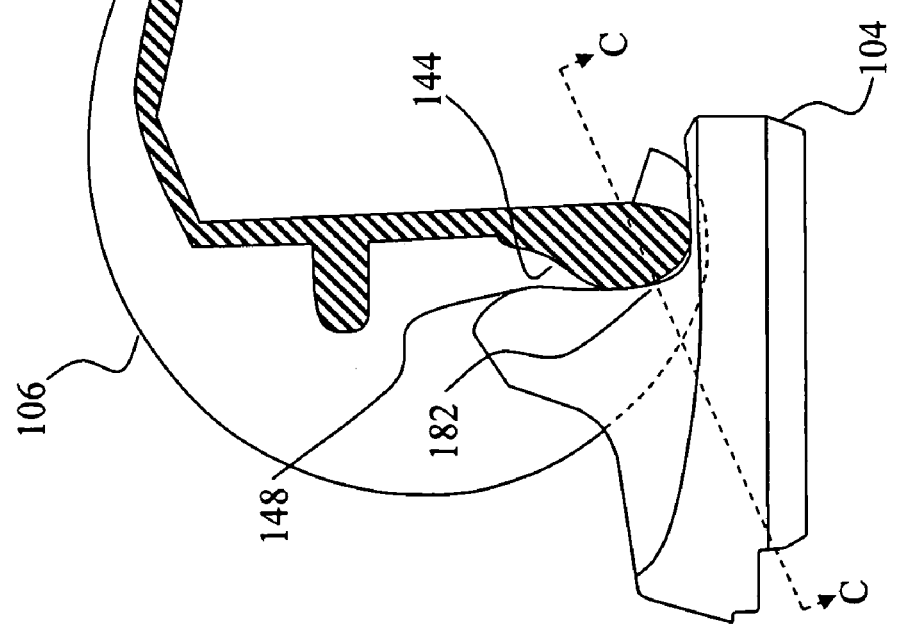
FIG. 12 depicts a sagittal cross sectional view of the femoral component of FIG. 5 and a sagittal plan view of the tibial bearing insert of FIG. 5 showing the contact region between the camming surfaces of the femoral component and the tibial bearing insert with the femoral component positioned at about 110 degrees of flexion on the tibial bearing insert.

Continued rotation of the femoral component 106 to about 110 degrees of flexion on the tibial bearing insert 104 results in the configuration of FIG. 12. At this rotation, the posterior cam 144 and the posterior camming portion 148 are in contact at the contact region 182. FIG. 13 depicts the shape of the posterior camming portion 148 and the shape of the posterior cam 144 at the contact region 182 taken along the line C-C.

In FIG. 13, the $R_c$ 184 of the posterior camming portion 148 has the same length as the $R_c$ 152 of FIG. 8. The length of the $R_c$ 184 may be modified to be longer or shorter than the $R_c$ 152 if desired. The $R_c$ 184, however, has an origin 186 which is positioned to the lateral side of the centerline 156. In one embodiment, the origin 186 is located 2.75 millimeters to the lateral side of the centerline 156. Additionally, the posterior cam 144 is formed with an $R_c$ 188 of the same length as the $R_c$ 158, although a longer or shorter length than the $R_c$ 158 may be selected, and the origin 190 of the $R_c$ 188 is positioned on the centerline 162. Accordingly, the shape of the posterior camming portion 148 and the posterior cam 144 maintain the femoral component 106 in rotation with respect to the tibial bearing insert 104 while providing substantially similar rollback of the femoral condyle elements 108 and 110 on the tibial bearing insert 104.

FIG. 14 depicts the femoral component 106 rotated to about 130 degrees of flexion on the tibial bearing insert 104. At this rotation, the posterior cam 144 and the posterior camming portion 148 are in contact at the contact region 192. FIG. 15 depicts the shape of the posterior camming portion 148 and the shape of the posterior cam 144 at the contact region 192 taken along the line D-D of FIG. 14.

In FIG. 15, the $R_c$ 194 of the posterior camming portion 148 has the same length as the $R_c$ 152 of FIG. 8. The length of the $R_c$ 194 may be modified to be longer or shorter than the $R_c$ 152 if desired. The $R_c$ 194, however, has an origin 196 which is positioned to the lateral side of the centerline 156. In one embodiment, the origin 196 is located 4 millimeters to the lateral side of the centerline 156. Additionally, the posterior cam 144 is formed with an $R_c$ 198 of the same length as the $R_c$ 158, although a longer or shorter length than the $R_c$ 158 may be selected, and the origin 200 of the $R_c$ 198 is positioned on the centerline 162. Accordingly, the shape of the posterior camming portion 148 and the posterior cam 144 maintain the femoral component 106 in rotation with respect to the tibial bearing insert 104 while providing substantially similar rollback of the femoral condyle elements 108 and 110 on the tibial bearing insert 104.

Figure 16:
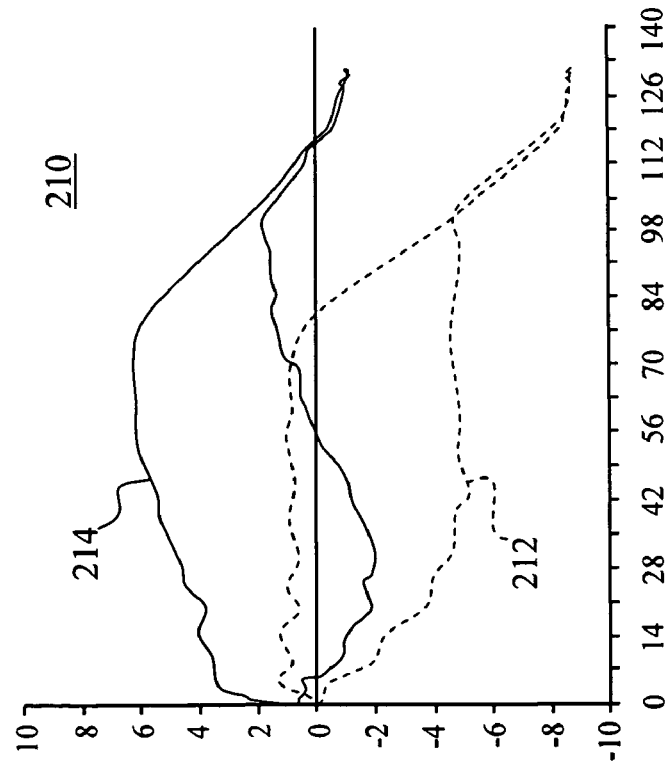
FIG. 16 shows a graph of the condylar low points during a deep knee bending simulation using the knee replacement system of FIG. 5.

A deep knee bending simulation was conducted with a model of the femoral component 106 on the tibial bearing insert 104 to verify the rollback and rotational characteristics of this embodiment. LMKS Modeling Results for the femoral component 106 on the tibial bearing insert 104 are shown in FIG. 16 wherein the graph 210 includes lines 212 and 214 which show the estimated low (tangency) points for the lateral condylar surface 110 and the medial condylar surface 108, respectively, of the femoral component 106 on the tibial bearing insert 104. The lower portion of the lines 212 and 214 were generated as the components were moving into flexion. Both of the lines 212 and 214 initially track posteriorly (downwardly as viewed in the FIG. 16) between 0 and about 35 degrees of flexion. Thus, the femoral component 106 is moving posteriorly or "rolling back" on the tibial bearing insert 104.

Figure 17:
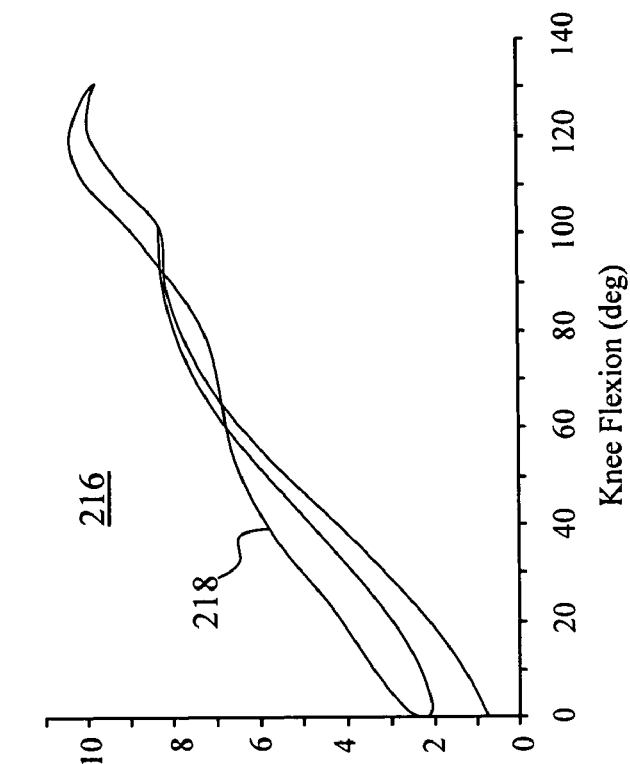
FIG. 17 shows a graph of the internal-external rotation ($\phi_{i-e}$) of the tibia with respect to the femoral component during the deep knee bending simulation using the knee replacement system of FIG. 5.

The amount of rollback of the lateral condylar surface 110 and the medial condylar surface 108 between 0 degrees and 35 degrees of flexion is not the same. This indicates that the femoral component 106 is rotating. This is supported by the LMKS Modeling Results for the femoral component 106 on the tibial bearing insert 104 shown in the graph 216 of FIG. 17 wherein the line 218 of the graph 216 identifies the $\phi_{i-e}$ of the femoral component 106 on the tibial bearing insert 104. The graph 216 reveals that at about 35 degrees of flexion, the $\phi_{i-e}$ for the femoral component 106 on the tibial bearing insert 104 is about 3 degrees.

Returning to FIG. 16, beyond about 35 degrees of flexion, the line 214 shows that the medial condyle 108 drifts slightly anteriorly on the tibial bearing insert 104 to about 80 degrees of flexion while the line 212 indicates that the lateral condyle 110 maintains the same location on the tibial bearing insert 104 through about 105 degrees of flexion. Thus, the medial condyle 108 (line 214) appears to be exhibiting negative slip while the lateral condyle 110 (line 212) is slipping at a relatively constant rate of pure slip. Accordingly, FIG. 16 indicates that the $\phi_{i-e}$ should increase between about 35 degrees of flexion and about 105 degrees of flexion. The graph 216 supports this as the $\phi_{i-e}$ for the femoral component 106 on the tibial bearing insert 104 changes from about 3 degrees at 35 degrees of flexion to almost 8 degrees at 80 degrees of flexion.

Beyond 80 degrees of flexion, the medial condyle 108 (line 214) remains relatively constant before moving posteriorly from about 105 degrees of flexion to 130 degrees of flexion. The lateral condyle 110 (line 212) remains constant to about 105 degrees of flexion and then moves rapidly posteriorly. This indicates that from about 80 degrees of flexion to about 105 degrees of flexion the $\phi_{i-e}$ for the femoral component 106 on the tibial bearing insert 104 should be relatively constant followed by an increase in $\phi_{i-e}$ through 130 degrees of flexion. A review of the LMKS Modeling Results for the femoral component 106 on the tibial bearing insert 104 confirms the expected $\phi_{i-e}$.

Accordingly, the asymmetrically shaped posterior cam 144 and posterior camming portion 148, which initially contact one another at about 70 degrees of flexion, provide for additional rollback and rotation between the femoral component 106 and the tibial bearing insert 104.

Figure 18:
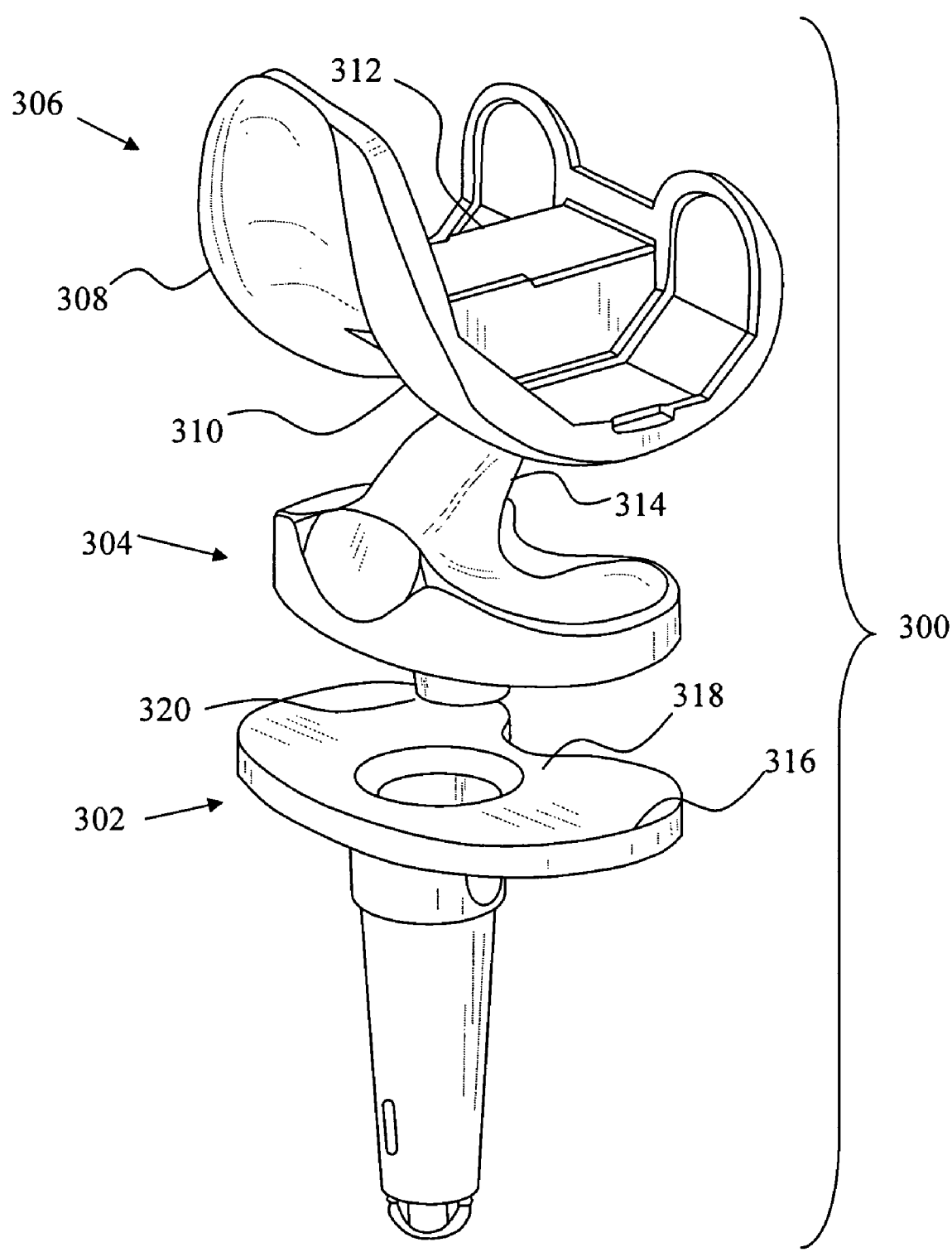
FIG. 18 depicts an exploded perspective view of an alternative knee prosthesis system including a tibial component with a rotating platform and a femoral component in accordance with principles of the invention.

FIG. 18 depicts an alternative knee replacement system 300. The knee replacement system 300 includes a tibial tray 302, a tibial bearing insert 304 and a femoral component 306 having two femoral condyle elements 308 and 310. A cam compartment 312 is located between the femoral condyle elements 308 and 310 and a spine 314 extends upwardly from the tibial bearing insert 304. The tibial tray 302, the tibial bearing insert 304 and the femoral component 306 are substantially identical to the corresponding components of the knee replacement system 100. A difference between the knee replacement system 300 and the knee replacement system 100 is that the tibial bearing insert 304 is configured to rotate on the tibial superior bearing surface 316 of the tibial tray 302. To this end, the tibial tray 302 includes a coupling member 318 for rotatably receiving a coupling member 320 of the tibial bearing insert 304.

FIG. 19 depicts a cross sectional view of the femoral component 306 taken through the cam compartment 312 and a side plan view of the tibial bearing insert 304. An anterior cam 342 and a posterior cam 344 are located within the cam compartment 312. The spine 314 includes an anterior camming portion 346 and a posterior camming portion 348. The anterior cam 342 is configured with the anterior camming portion 346 to preclude undesired posterior slippage when the femoral component 306 is positioned on the tibial bearing insert 304.

The femoral component 306 is depicted in FIG. 19 in full extension. The low or tangency point of the femoral component 306 is identified as condylar dwell point 350. The condylar dwell point 350 and the condylar dwell point 352 for the condyle element 310, shown projected onto the tibial superior bearing surface 316 in FIG. 20, define a dwell axis 354. The dwell axis 354 intersects the centerline 356 of the tibial superior bearing surface 316 at a point defined herein as the "dwell point" 358. The dwell point 358 is located anteriorly and medially to the center of the coupling member 318 which, along with the coupling member 320, defines an axis of rotation 322 for the tibial bearing insert 304 (see also FIG. 21). The axis of rotation 322 is offset from the central axis 324 of the tibial tray 302 in a lateral and posterior direction. In one embodiment, the axis of rotation 322 is offset from the dwell point 358 of the tibial tray 302 by about 0.317 inches laterally and about 0.317 inches posteriorly.

Figure 22:
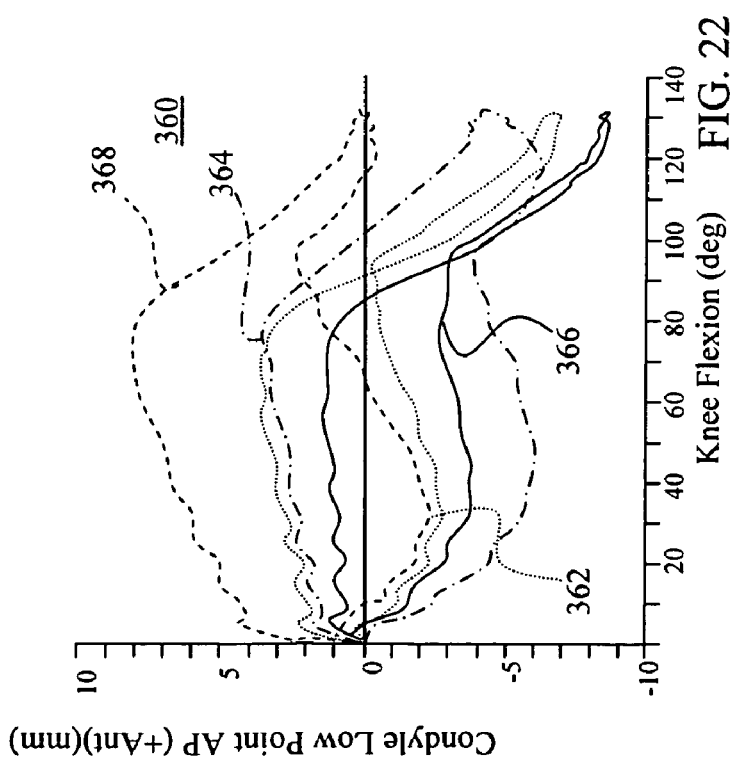
FIG. 22 shows a graph of the results of a deep knee bending simulation using the knee replacement system of FIG. 18 with an axis of rotation of the tibial bearing insert positioned about 0.317 inches posterior to the dwell axis of the system and about 0.317 inches lateral to the centerline of the tibial bearing insert.

A deep knee bending simulation was conducted on the femoral component 306 on the tibial bearing insert 304 to verify the rollback and rotational characteristics of this embodiment. LifeMod/KneeSim Modeling Results for the simulation are shown in FIG. 22 wherein the graph 360 includes lines 362 and 364 which show the estimated low (tangency) points for the lateral condylar surface 310 and the medial condylar surface 308, respectively, of the femoral component 306 on the tibial bearing insert 304. The graph 360 further includes lines 366 and 368 which show the estimated low (tangency) points for the lateral condylar surface 310 and the medial condylar surface 308, respectively, of the femoral component 306 with respect to the tibial tray 302. The lower portion of the lines 362, 364, 366, and 368 were generated as the components were moving into flexion.

The graph 360 generally shows the femoral component 306 is moving posteriorly or "rolling back" on the tibial bearing insert 304 until about 40 degrees of flexion and again from about 95 degrees of flexion to 130 degrees of flexion.

Figure 23:
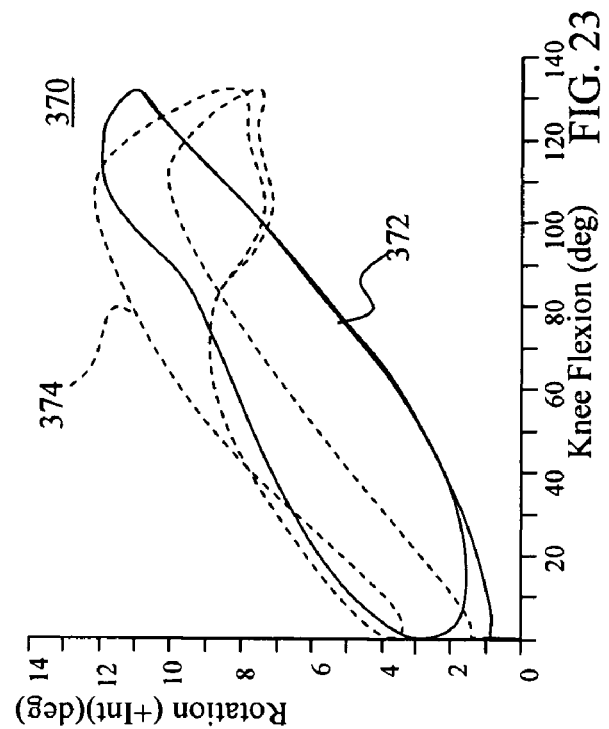
FIG. 23 shows a graph of the internal-external rotation ($\phi_{i-e}$) of the tibia with respect to the femoral component during the deep knee bending simulation of FIG. 22 along with the rotation of the tibial bearing insert with respect to the tibia.

The graph 370 of FIG. 23 includes the line 372 which identifies the $\phi_{i-e}$ of the femoral component 306 with respect to the tibia. The line 372 reveals that between 0 degrees of flexion and about 130 degrees of flexion, the $\phi_{i-e}$ for the femoral component 306 with respect to the tibia is steadily increasing to about 11 degrees. The graph 370 further includes a line 374 which identifies the rotation of the tibial bearing insert 304 with respect to the tibia. The line 374 reveals that between 0 degrees of flexion and about 110 degrees of flexion, there is a steady increase in the rotation of the tibial bearing insert 104 with respect to the tibia to about 10 degrees of rotation, followed by a slight decrease through 130 degrees of flexion.

Thus, the rotation of the tibial bearing insert 304 with respect to the tibia was greater than the $\phi_{i-e}$ for the femoral component 306 until about 120 degrees of flexion with the maximum difference in rotation between the femoral component 306 and the tibial bearing insert 304 about 3 degrees at about 60 degrees of flexion. On subsequent cycles, the rotation of the tibial bearing insert 304 with respect to the tibia was generally higher, with the maximum difference in rotation between the femoral component 306 and the tibial bearing insert 304 about 6 degrees at about 60 degrees of flexion.

Accordingly, an asymmetrically shaped posterior cam and posterior camming portion as described above, which initially contact one another at about 70 degrees of flexion, provide for additional rollback and rotation between a femoral component and a tibial bearing insert which is fixed or a tibial bearing insert which is rotatable.

Figure 25:
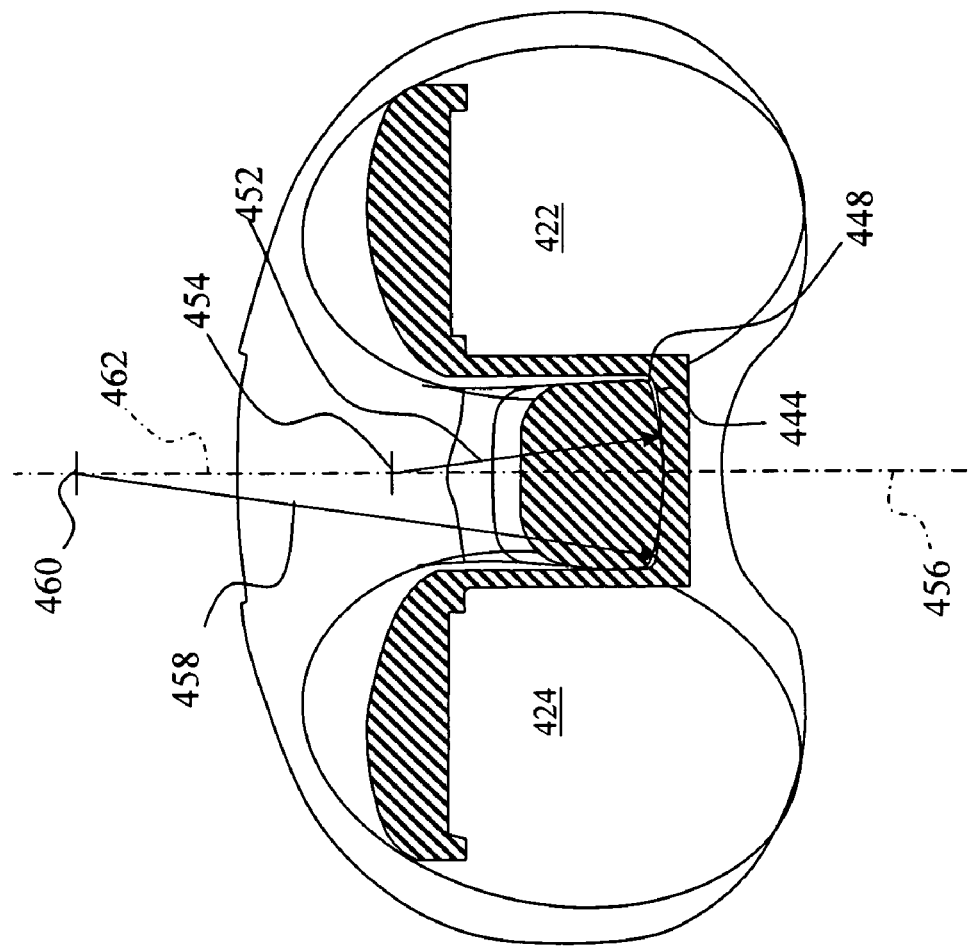
FIG. 25 depicts a medio-lateral cross sectional view of the configuration of FIG. 24 taken along the line E-E of FIG. 24 showing the origins of the radius of curvature of the camming surfaces of the femoral component and the tibial bearing insert to be located on the centerlines of the respective component.
Figure 24:
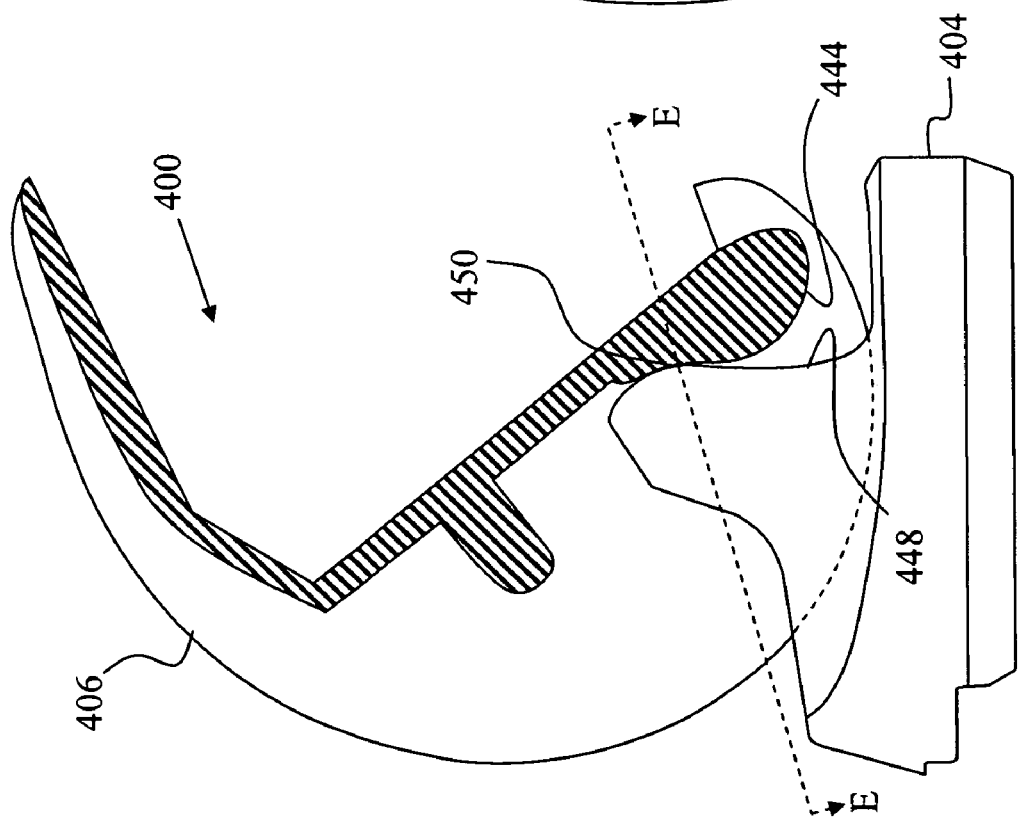
FIG. 24 depicts a sagittal cross sectional view of an alternative femoral component and a sagittal plan view of an alternative tibial bearing insert showing the contact region between the camming surfaces of the femoral component and the tibial bearing insert with the femoral component positioned at about 70 degrees of flexion on the tibial bearing insert.

The asymmetry which provides for a gradual rotation and increased rollback need not be introduced in the tibial component. By way of example, FIG. 24 depicts a knee replacement system 400 with components substantially identical to the corresponding components of the knee replacement system 100 to which reference may be made for further identification of the components. In FIG. 24, femoral component 406 is rotated to about 70 degrees of flexion on the tibial bearing insert 404. At this rotation, the posterior cam 444 and the posterior camming portion 448 are in contact at the contact region 450. FIG. 25 depicts the shape of the posterior camming portion 448 and the shape of the posterior cam 444 at the contact region 450 taken along the line E-E of FIG. 24 which extends from a medial portion of the camming portion 448 and the posterior cam 444 to a lateral portion of the camming portion 448 and the posterior cam 444 in a mediolateral plane.

The posterior camming portion 448 is formed on a radius of curvature ($R_c$) 452 having an origin 454 on the centerline 456 of the tibial bearing insert 404. In one embodiment, the $R_c$ 452 may be about 20 millimeters. The posterior cam 444 is formed on a radius of curvature ($R_c$) 458 having an origin 460 on the centerline 462 of the femoral component 106. In one embodiment, the $R_c$ 458 may be about 40 millimeters. At about 70 degrees of flexion, the centerline 456 of the tibial bearing insert 404 and the centerline 462 of the femoral component 406 are substantially aligned. Thus, the origin 454 and the origin 460 are substantially aligned. Accordingly, the predominant effect of the contact between the posterior cam 444 and the posterior camming portion 448 is the prevention of anterior movement of the femoral component 406 on the tibial bearing insert 404.

Continued rotation of the femoral component 406 to about 90 degrees of flexion on the tibial bearing insert 404 results in the configuration of FIG. 26. At this rotation, the posterior cam 444 and the posterior camming portion 448 are in contact at the contact region 470. FIG. 27 depicts the shape of the posterior camming portion 448 and the shape of the posterior cam 444 at the contact region 470 taken along the line F-F of FIG. 26.

In FIG. 27, the $R_c$ 472 of the posterior camming portion 148 has the same length as the $R_c$ 452 of FIG. 25. The $R_c$ 472 also has an origin 474 which is positioned on the centerline 456. The posterior cam 444 is formed with an $R_c$ 476 of the same length as the $R_c$ 458. The origin 478 of the $R_c$ 476, however, is positioned to the medial side of the centerline 462. In one embodiment, the origin 478 of the $R_c$ 476 is positioned 1 millimeter to the medial side of the centerline 462. Accordingly, the shape of the posterior camming portion 448 and the posterior cam 444 cause a rotational force in the direction of the arrow 480. The lateral condyle, femoral condyle element 410 in this embodiment, is thus forced to move posteriorly at a rate greater than the medial condyle (femoral condyle element 408).

The result of the forces acting upon the femoral component 406 is rotation of the femoral component 406 with respect to the tibial bearing insert 404 as shown in FIG. 28. In FIG. 28, the centerline 462 has rotated in a counterclockwise direction from the centerline 456. Additionally, opposing faces of the posterior camming portion 448 and the posterior cam 444, in contrast to the configuration shown in FIG. 27, are more aligned with each other.

The movement of the origins of the $R_c$ for the posterior cam 444 is done incrementally along the contact surfaces of the posterior cam 444 between the contact region 450 and the contact region 470. This provides a smooth rotational movement of the femoral component 406 on the tibial bearing insert 404 from the alignment of FIG. 25 to the alignment of FIG. 28. The precise amount of rotation and rollback may be adjusted by modifying the offset of the origins.

Continued rotation of the femoral component 406 to about 110 degrees of flexion on the tibial bearing insert 404 results in the configuration of FIG. 29. At this rotation, the posterior cam 444 and the posterior camming portion 448 are in contact at the contact region 482. FIG. 30 depicts the shape of the posterior camming portion 448 and the shape of the posterior cam 444 at the contact region 482 taken along the line G-G.

In FIG. 30, the $R_c$ 484 of the posterior camming portion 448 has the same length as the $R_c$ 452 of FIG. 25. The $R_c$ 484 further has an origin 486 which is positioned on the centerline 456. While the posterior cam 444 is formed with an $R_c$ 488 of the same length as the $R_c$ 458, the origin 490 of the $R_c$ 488 is positioned to the medial side of the centerline 462. In one embodiment, the origin 490 of the $R_c$ 488 is positioned 2 millimeters to the medial side of the centerline 462. Accordingly, the shape of the posterior camming portion 448 and the posterior cam 444 maintain the femoral component 406 in rotation with respect to the tibial bearing insert 404 while providing substantially similar rollback of the femoral condyle elements 408 and 410 on the tibial bearing insert 404.

FIG. 31 depicts the femoral component 406 rotated to about 130 degrees of flexion on the tibial bearing insert 404. At this rotation, the posterior cam 444 and the posterior camming portion 448 are in contact at the contact region 492. FIG. 32 depicts the shape of the posterior camming portion 448 and the shape of the posterior cam 444 at the contact region 492 taken along the line H-H of FIG. 31.

In FIG. 32, the $R_c$ 494 of the posterior camming portion 448 has the same length as the $R_c$ 452 of FIG. 25. Additionally, the $R_c$ 494 has an origin 496 which is positioned on the centerline 456. While the posterior cam 444 is formed with an $R_c$ 498 of the same length as the $R_c$ 458, however, the origin 500 of the $R_c$ 498 is positioned to the medial side of the centerline 462. In one embodiment, the origin 500 of the $R_c$ 498 is positioned about 3.5 millimeters to the medial side of the centerline 462. Accordingly, the shape of the posterior camming portion 448 and the posterior cam 444 maintain the femoral component 406 in rotation with respect to the tibial bearing insert 404 while providing substantially similar rollback of the femoral condyle elements 408 and 410 on the tibial bearing insert 404.

Accordingly, providing an asymmetry as described above either on the tibial component or on the femoral component or with a combination of the two components, provides for additional rollback and rotation between a femoral component and a tibial bearing insert which is fixed or a tibial bearing insert which is rotatable.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

The invention claimed is:

1. A prosthetic joint comprising:
a proximal tibial camming portion extending between a lateral portion of a posterior tibial cam of a tibial component and a medial portion of the posterior tibial cam in a first medio-lateral plane, the proximal tibial camming portion defined by sweeping a first radius of curvature in the first medio-lateral plane, the first radius of curvature having a first origin;
a distal tibial camming portion extending between the lateral portion of the posterior tibial cam and the medial portion of the posterior tibial cam in a second medio-lateral plane, the distal tibial camming portion defined by sweeping a second radius of curvature in the second medio-lateral plane, the second radius of curvature having a second origin;
an anterior femoral camming portion extending between a lateral portion of a posterior femoral cam of a femoral component and a medial portion of the posterior femoral cam in the first medio-lateral plane, the anterior femoral camming portion defined by sweeping a third radius of curvature in the first medio-lateral plane, the third radius of curvature having a third origin;
a posterior femoral camming portion extending between the lateral portion of the posterior femoral cam and the medial portion of the posterior femoral cam in the second medio-lateral plane and defined by sweeping a fourth radius of curvature in the second medio-lateral plane, the fourth radius of curvature having a fourth origin,
wherein the second origin is closer to the lateral tibial portion than the first origin, or the fourth origin is closer to the medial femoral portion than the third origin;
wherein the tibial component has a centerline dividing the tibial component into medial and lateral bearing surfaces,
and wherein at least one origin of the first, second, third, or fourth origin is medially or laterally offset from the centerline of the tibial component when the centerline is projected onto, and the at least one origin is viewed in its respective medio-lateral plane.

2. The prosthetic joint of claim 1, wherein the prosthetic joint is configured such that the proximal tibial camming portion contacts the anterior femoral camming portion during flexion and the distal tibial camming portion contacts the posterior femoral camming portion during flexion.

3. The prosthetic joint of claim 1, wherein the prosthetic joint is configured such that the proximal tibial camming portion contacts the anterior femoral camming portion at about 70 degrees of flexion and the distal tibial camming portion contacts the posterior femoral camming portion at about 130 degrees of flexion.

4. The prosthetic joint of claim 1, further comprising:
an intermediate tibial camming portion extending between the lateral portion of the tibial cam and the medial portion of the tibial cam within a third medio-lateral plane, the intermediate tibial camming portion defined by sweeping a fifth radius of curvature in the third medio-lateral plane, the fifth radius of curvature having a fifth origin; and
an intermediate femoral camming portion extending between the lateral portion of the femoral cam and the medial portion of the femoral cam within the third medio-lateral plane, the intermediate femoral camming portion defined by sweeping a sixth radius of curvature in the third medio-lateral plane, the sixth radius of curvature having a sixth origin,
wherein (i) the fifth origin is closer to the lateral tibial portion than the first origin and farther from the lateral tibial portion than the second origin, or (ii) the sixth origin is closer to the medial femoral portion than the third origin and farther from the lateral femoral portion than the fourth origin.

5. The prosthetic joint of claim 4, wherein:
the first origin is located proximate to the centerline of the tibial component when the centerline is projected onto the first medio-lateral plane;
the second origin is spaced apart from the first origin in the lateral direction by about 4 millimeters when the second origin is projected onto the first medio-lateral plane;
the fifth origin is spaced apart from the first origin in the lateral direction by about 3 millimeters when the fifth origin is projected onto the first medio-lateral plane; the proximal tibial camming portion contacts the anterior femoral camming portion at about 70 degrees of flexion;
the intermediate tibial camming portion contacts the intermediate femoral camming portion at about 110 degrees of flexion; and
the distal tibial camming portion contacts the posterior femoral camming portion at about 130 degrees of flexion.

6. The prosthetic joint of claim 4, wherein:
the third origin is located proximate to the centerline of the tibial component when the third origin is projected onto the first medio-lateral plane;
the fourth origin is spaced apart from the first origin in the lateral direction by at least 3 millimeters when the fourth origin is projected onto the first medio-lateral plane;
the sixth origin is spaced apart from the third origin in the lateral direction by about 2 millimeters when the sixth origin is projected onto the first medio-lateral plane;
the proximal tibial camming portion contacts the anterior femoral camming portion at about 70 degrees of flexion;
the intermediate tibial camming portion contacts the intermediate femoral camming portion at about 110 degrees of flexion; and
the distal tibial camming portion contacts the posterior femoral camming portion at about 130 degrees of flexion.

7. The prosthetic joint of claim 1, further comprising:
a medial tibial articulating portion that articulates with a medial condylar articulating portion with a first condylar dwell point; and
a lateral tibial articulating portion that articulates with a lateral condylar articulating portion with a second condylar dwell point,
wherein the medial tibial articulating portion and the lateral tibial articulating portion are rotatable on a tibial plateau about an axis of rotation that intersects the tibial plateau at about 90 degrees,
and the axis of rotation intersects the tibial plateau at a location (i) posterior to a dwell axis including the first condylar dwell point and the second condylar dwell point,
and (ii) lateral to the centerline of the tibial component when the centerline is projected onto the first medio-lateral plane plateau.

8. The prosthetic joint of claim 7, wherein the axis of rotation intersects the tibial plateau at a location (i) about 0.317 inches posterior to the dwell axis, and (ii) about 0.317 inches lateral to the centerline of the tibial component when the centerline is projected onto the first medio-lateral plane.

9. The prosthetic joint of claim 1, wherein (i) the first and the second radius of curvature have the same length, and (ii) the third and the fourth radius of curvature have the same length.

10. A knee prosthesis comprising:
a tibial cam of a tibial component including a posterior camming surface portion defined by sweeping each of a plurality of tibial radii of curvature in a respective one of a plurality of medio-lateral planes generally perpendicular to the camming surface, each of the plurality of tibial radii of curvature having an origin, each of the origins of the plurality of tibial radii of curvature spaced apart from the other in the medio-lateral direction; and
a posterior femoral cam of a femoral component including a distal camming surface portion defined by a plurality of femoral radii of curvature, each of the plurality of femoral radii of curvature located in a respective one of the plurality of medio-lateral planes;
wherein the tibial component has a centerline dividing the tibial component into medial and lateral bearing surfaces,
and wherein at least one origin is medially or laterally offset from the centerline of the tibial component when the centerline is projected onto, and the at least one origin is viewed in its respective medio-lateral plane.

11. The knee prosthesis of claim 10, wherein:
each origin that is located distally from an other origin of the plurality of tibial radii of curvature is positioned laterally from the other origin.

12. The knee prosthesis of claim 11 wherein:
a first origin of a first of the plurality of tibial radii of curvature is located proximate to the centerline of the tibial component when the first origin and the centerline are projected onto a first medio-lateral plane;
a second origin of a second of the plurality of tibial radii of curvature is spaced apart from the first origin of the first of the plurality of tibial radii of curvature in the lateral direction by about 1.5 millimeters when the second origin is projected onto the first medio-lateral plane;
a third origin of a third of the plurality of tibial radii of curvature is spaced apart from the first origin of the first of the plurality of tibial radii of curvature in the lateral direction by about 3.75 millimeters when the third origin is projected onto the first medio-lateral plane; and
a fourth origin of a fourth of the plurality of tibial radii of curvature is spaced apart from the first origin of the first of the plurality of tibial radii of curvature in the lateral direction by about 4 millimeters when the third origin is projected onto the first medio-lateral plane, wherein
the posterior camming surface contacts the distal camming surface (i) at about 70 degrees of flexion at a location defined by a first of the plurality of femoral radii of curvature and the first of the plurality of tibial radii of curvature, (ii) at about 90 degrees of flexion at a location defined by a second of the plurality of femoral radii of curvature and the second of the plurality of tibial radii of curvature, (iii) at about 110 degrees of flexion at a location defined by a third of the plurality of femoral radii of curvature and the third of the plurality of tibial radii of curvature, and (iv) at about 130 degrees of flexion at a location defined by a fourth of the plurality of femoral radii of curvature and the fourth of the plurality of tibial radii of curvature.

13. The knee prosthesis of claim 11 wherein:
a first origin of a first of the plurality of tibial radii of curvature is located proximate to the centerline of the tibial component when the first origin and the centerline are projected onto a first medio-lateral plane;
a second origin of a second of the plurality of tibial radii of curvature is spaced apart from the first origin of the first of the plurality of tibial radii of curvature in the lateral direction by about 4 millimeters when the second origin is projected onto the first medio-lateral plane, wherein
the posterior camming surface contacts the distal camming surface (i) at about 70 degrees of flexion at a location defined by a first of the plurality of femoral radii of curvature and the first of the plurality of tibial radii of curvature, and (ii) at about 130 degrees of flexion at a location defined by a second of the plurality of femoral radii of curvature and the second of the plurality of tibial radii of curvature.

14. The knee prosthesis of claim 13 wherein each origin located distally from an other origin of the plurality of tibial radii of curvature is positioned incrementally laterally from the other origin.

15. The knee prosthesis of claim 10, wherein each of the plurality of femoral radii of curvature have a respective origin, each respective origin spaced apart from the other respective origins of the other of the plurality of femoral radii of curvature in the medio-lateral direction.

16. The knee prosthesis of claim 15, wherein each of the respective origins located posteriorly from an other of the respective origins is positioned incrementally laterally from the other of the respective origins.

17. The knee prosthesis of claim 10, further comprising:
a medial tibial articulating portion that articulates with a medial condylar articulating portion with a first condylar dwell point; and
a lateral tibial articulating portion that articulates with a lateral condylar articulating portion with a second condylar dwell point, wherein
the medial tibial articulating portion and the lateral tibial articulating portion are rotatable on a tibial plateau about an axis of rotation that intersects the tibial plateau at about 90 degrees, and
the axis of rotation intersects the tibial plateau at a location (i) posterior to a dwell axis including the first condylar dwell point and the second condylar dwell point, and (ii) lateral to the centerline of the tibial component when the centerline is projected onto the tibial plateau.

18. The knee prosthesis of claim 17, wherein the axis of rotation intersects the tibial plateau at a location (i) about 0.317 inches posterior to the dwell axis, and (ii) about 0.317 inches lateral to the centerline of the tibial component when the centerline is projected onto the tibial plateau.

19. A knee prosthesis comprising:
a tibial cam of a tibial component including a posterior camming surface portion defined by a plurality of radii of curvature, each of the plurality of tibial radii of curvature located in an associated one of a plurality of medio-lateral planes perpendicular to the posterior camming surface; and
a posterior femoral cam of a femoral component including a distal camming surface portion defined by sweeping a plurality of radii of curvature, in a respective one of the plurality of medio-lateral planes, each of the plurality of femoral radii of curvature having an origin, each origin spaced apart from the other origins in the medio-lateral direction;
wherein the tibial component has a centerline dividing the tibial component into medial and lateral bearing surfaces,
and wherein at least one origin is medially or laterally offset from the centerline of the tibial component when the centerline is projected onto, and the at least one origin is viewed in its respective medio-lateral plane.

20. The knee prosthesis of claim 19, wherein:
each origin located posteriorly from another origin is positioned medially from the other origin.

21. The knee prosthesis of claim 20 wherein:
a first origin of a first of the plurality of femoral radii of curvature is located proximate to the centerline of the femoral component when the first origin and the centerline are projected onto a first medio-lateral plane;
a second origin of a second of the plurality of femoral radii of curvature is spaced apart from the first origin in the medial direction by about 1 millimeter when the second origin is projected onto the first medio-lateral plane;
a third origin of a third of the plurality of femoral radii of curvature is spaced apart from the first origin in the medial direction by about 2 millimeters when the third origin is projected onto the first medio-lateral plane; and
a fourth origin of a fourth of the plurality of femoral radii of curvature is spaced apart from the first origin in the medial direction by at least 3 millimeters when the fourth origin is projected onto the first medio-lateral plane wherein
the posterior camming surface contacts the distal camming surface (i) at about 70 degrees of flexion at a location defined by the first of the plurality of femoral radii of curvature and a first of the plurality of tibial radii of curvature, (ii) at about 90 degrees of flexion at a location defined by the second of the plurality of femoral radii of curvature and a second of the plurality of tibial radii of curvature, (iii) at about 110 degrees of flexion at a location defined by the third of the plurality of femoral radii of curvature and a third of the plurality of tibial radii of curvature, and (iv) at about 130 degrees of flexion at a location defined by the fourth of the plurality of femoral radii of curvature and a fourth of the plurality of tibial radii of curvature.

22. The knee prosthesis of claim 20 wherein:
a first origin of a first of the plurality of femoral radii of curvature is located proximate to the centerline of the femoral component when the first origin and the centerline are projected onto a first medio-lateral plane; and
a second origin of a second of the plurality of femoral radii of curvature is spaced apart from the first origin in the medial direction by about 3.5 millimeters when the second origin is projected onto the first medio-lateral plane, wherein
the posterior camming surface contacts the distal camming surface (i) at about 70 degrees of flexion at a location defined by the first of the plurality of femoral radii of curvature and a first of the plurality of tibial radii of curvature, and (ii) at about 130 degrees of flexion at a location defined by the second of the plurality of femoral radii of curvature and a second of the plurality of tibial radii of curvature.

23. The knee prosthesis of claim 20 wherein each origin located posteriorly from an other origin is positioned incrementally medially from the other origin.

* * * * *